(12) United States Patent
Chilkoti et al.

(10) Patent No.: US 9,592,303 B2
(45) Date of Patent: Mar. 14, 2017

(54) ENZYME-CATALYZED SYNTHESIS OF SITE-SPECIFIC AND STOICHIOMETRIC BIOMOLECULE-POLYMER CONJUGATES

(71) Applicant: Duke University, Durham, NC (US)

(72) Inventors: Ashutosh Chilkoti, Durham, NC (US); Yizhi Qi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/894,731

(22) PCT Filed: May 30, 2014

(86) PCT No.: PCT/US2014/040319
§ 371 (c)(1),
(2) Date: Nov. 30, 2015

(87) PCT Pub. No.: WO2014/194244
PCT Pub. Date: Dec. 4, 2014

(65) Prior Publication Data
US 2016/0122451 A1     May 5, 2016

Related U.S. Application Data

(60) Provisional application No. 61/828,873, filed on May 30, 2013.

(51) Int. Cl.
*A61K 47/48* (2006.01)
*C07K 1/107* (2006.01)
*C08F 122/10* (2006.01)

(52) U.S. Cl.
CPC ...... *A61K 47/48176* (2013.01); *C07K 1/1077* (2013.01); *C08F 122/105* (2013.01)

(58) Field of Classification Search
CPC .......... C08F 122/105; A61K 47/48176; C07K 1/1077
See application file for complete search history.

(56) References Cited

U.S. PATENT DOCUMENTS

| | | | |
|---|---|---|---|
| 4,554,101 A | 11/1985 | Hopp | |
| 5,580,859 A | 12/1996 | Felgner et al. | |
| 5,676,646 A | 10/1997 | Hofmann et al. | |
| 5,679,647 A | 10/1997 | Carson et al. | |
| 5,702,359 A | 12/1997 | Hofmann et al. | |
| 5,703,055 A | 12/1997 | Felgner et al. | |
| 6,068,650 A | 5/2000 | Hofmann et al. | |
| 6,096,020 A | 8/2000 | Hofmann | |
| 6,120,493 A | 9/2000 | Hofmann | |
| 6,150,148 A | 11/2000 | Nanda et al. | |
| 6,181,964 B1 | 1/2001 | Hoffmann et al. | |
| 6,192,270 B1 | 2/2001 | Hofmann et al. | |
| 6,207,749 B1 | 3/2001 | Mayes et al. | |
| 6,208,893 B1 | 3/2001 | Hofmann | |
| 6,216,034 B1 | 4/2001 | Hofmann et al. | |
| 6,233,482 B1 | 5/2001 | Hofmann et al. | |
| 6,241,701 B1 | 6/2001 | Hofmann | |
| 6,302,874 B1 | 10/2001 | Zhang et al. | |
| 6,623,950 B1 | 9/2003 | Osten et al. | |
| 7,664,545 B2 | 2/2010 | Westersten et al. | |
| 8,497,356 B2 | 7/2013 | Chilkoti et al. | |
| 2006/0034796 A1 | 2/2006 | Ashwell et al. | |
| 2007/0087114 A1 | 4/2007 | Chilkoti et al. | |
| 2008/0181861 A1 | 7/2008 | Jiang et al. | |
| 2011/0294189 A1 | 12/2011 | Chilkoti et al. | |

FOREIGN PATENT DOCUMENTS

WO    WO 2007/108013    9/2007
WO    WO 2013/065009    5/2013

OTHER PUBLICATIONS

Antos et al., "Lipid Modification of Proteins through Sortase-Catalyzed Transpeptidation," J. Am. Chem. Soc. 2008, 130, 16338-16343.
Antos, J. M.; Chew, G.; Guimaraes, C. P.; Yoder, N. C.; Grotenbreg, G. M.; Popp, M. W.; Ploegh, H. L. J. Am. Chem. Soc. 2009, 131, 10800-10801.
Averick, S. S., A.; Park, S.; Konkolewicz, D.; Magenau, A. J. D.; Mehl, R. A.; Matyjaszewski, K. ACS Macro. Lett. 2012, 1, 6.
Axup, J.Y. et al., "Synthesis of site-specific antibody-drug conjugates using unnatural amino acids," Proc Natl Acad Sci USA, 2012, 109(40):16101-16106.
Bansal, R.; Post, E.; Proost, J. H.; de Jager-Krikken, A.; Poelstra, K.; Prakash, J. "PEGylation improves pharmacokinetic profile, liver uptake and efficacy of Interferon gamma in liver fibrosis," J. Control. Release 2011, 154, 233-240.
Bellucci, J.J et al., "Three-in-one chromatography-free purification, tag removal, and site-specific modification of recombinant protein fusions using sortase A and elastin-like polypeptides," Angew Chem Int Ed Engl, 2013, 52(13):3703-3708.
Boekhorst, J.; de Been, M. W.; Kleerebezem, M.; Siezen, R. J. "Genome-Wide Detection and Analysis of Cell Wall-Bound Proteins with LPxTG-Like Sorting Motifs," J. Bacteriol. 2005, 187, 4928-4934.
Bontempo et al., "Streptavidin as a Macroinitiator for Polymerization: In Situ Protein-Polymer Conjugate Formation," J. Am. Chem. Soc. 2005, 6508-6509.
Boyer, C.; Bulmus, V.; Liu, J.; Davis, T. P.; Stenzel, M. H.; Barner-Kowollik, C. "Well-Defined Protein-Polymer Conjugates via in Situ RAFT Polymerization," J. Am. Chem. Soc. 2007, 129, 7145-7154.
Brown, K. "Light Scattering: Principles and Development"; Oxford University Press: New York, 1996 1-8.
Broyer, R. M.; Grover, G. N.; Maynard, H. D. Chem. Commun. 2011, 47, 2212.
Carrico, I.S. et al., "Introducing genetically encoded aldehydes into proteins," Nat Chem Biol, 2007, 3(6):321-322.
Chen, I. et al., "Site-specific labeling of cell surface proteins with biophysical probes using biotin ligase," Nat Methods, 2005, 2(2):99-104.

(Continued)

*Primary Examiner* — Robert Jones, Jr.
(74) *Attorney, Agent, or Firm* — Michael Best & Friedrich LLP

(57) ABSTRACT

Methods for producing polypeptide-polymer conjugates include attachment of an initiator agent to a polypeptide specifically at the C-terminus of the polypeptide using a sortase enzyme and in situ polymerization of a polymer from the C-terminus. The polypeptide-polymer conjugates may have desirable pharmacological properties and may be used therapeutically.

18 Claims, 10 Drawing Sheets

(56) References Cited

OTHER PUBLICATIONS

Dasgupta, S. et al., "Isopeptide Ligation Catalyzed by Quintessential Sortase A: Mechanistic Cues From Cyclic and Branched Oligomers of Indolicidin," The Journal of Biological Chemistry, 2011, vol. 286, No. 27, pp. 23996-24006, Supplemental Information.
De, P.; Li, M.; Gondi, S. R.; Sumerlin, B. S. "Temperature-Regulated Activity of Responsive Polymer-Protein Conjugates Prepared by Grafting-from via RAFT Polymerization," J. Am. Chem. Soc. 2008, 130, 11288-11289.
Depp, V.; Alikhani, A.; Grammer, V.; Lele, B. S. "Native protein-initiated ATRP: A viable and potentially superior alternative to PEGylation for stabilizing biologics," Acta Biomater. 2009, 5, 560-569.
Donnelly et al., "DNA Vaccines." Ann Rev. Immunol., 1997, 15, 617-648.
Drucker et al., "The incretin system: glucagon-like peptide-1 receptor agonists and dipeptidyl peptidase-4 inhibitors in type 2 diabetes" Lancet, 2006, 368: 1696-1705.
Duan, J. et al., "Fibronectin type III domain based monobody with high activity," Biochemistry, 2007 46(44):12656-12664.
Duncan, R. "Polymer conjugates as anticancer nanomedicines," Nat. Rev. Cancer 2006, 6, 688-701.
Gaberc-Porekar, V.; Zore, I.; Podobnik, B.; Menart, V. "Obstacles and pitfalls in the PEGylation of therapeutic proteins," Curr. Opin. Drug Discov. Devel. 2008, 11, 242-250.
Gao et al., "In situ growth of a stoichiometric PEG-like conjugate at a protein's N-terminus with significantly improved pharmacokinetics," A. Proc. Natl. Acad. Sci. 2009, 36, 15231-15236.
Gao, W., et al., "In situ growth of a PEG-like polymer from the C terminus of an intein fusion protein improves pharmacokinetics and tumor accumulation" PNAS Early Edition, 2010, vol. 107, 1-6.
Ge et al., "Self-Cleavable Stimulus Responsive Tags for Protein Purification without Chromatography" J. Am. Chem. Soc., 2005, 127: 11228-11229.
Green et al., "Novel dipeptidyl peptidase IV resistant analogues of glucagon-like peptide-1(7-36)amide have preserved biological activities in vitro conferring improved glucose-lowering action in vivo" J. of Mol. Endocrin., 2003, 31(3): 529-540.
Gregoriadis, Liposome Technology, vols. Ito III (2nd ed. 1993).
Grover et al., "Protein-Polymer Conjugates: Synthetic Approaches by Controlled Radical Polymerizations & Interesting Applications", Curr Opin Chem Bioi., Dec. 2010; 14(6): 818-827.
Hamidi, M.; Azadi, A.; Rafiei, P. "Pharmacokinetic Consequences of Pegylation," Drug Deliv. 2006, 13, 399-409.
Hassouneh, W., et al., "Elastin-like Polypeptides as a Purification Tag for Recombinant Proteins" Curr Protoc Protein Sci. Aug. 2010 ; Chapter: Unit-6.11, (20 pages).
Heredia, K. L.; Bontempo, D.; Ly, T.; Byers, J. T.; Halstenber, S.; Maynard, H. D. "In Situ Preparation of Protein—"Smart" Polymer Conjugates with Retention of Bioactivity," J. Am. Chem. Soc. 2005, 127, 16955-16960.
Ilangovan et al., "Structure of sortase, the transpeptidase that anchors proteins to the cell wall of Staphylococcus aureus," Proc. Natl. Acad. Sci. 2001, 98, 6056-6061.
Junutula, J.R. et al., "Site-specific conjugation of a cytotoxic drug to an antibody improves the therapeutic index," Nat Biotechnol, 2008, 26(8):925-932.
Keller, A. N., A. I.; Kolker, E.; Aebersold, R. "Empirical Statistical Model to Estimate the Accuracy of Peptide Identifications Made by MS/MS and Database Search," Anal Chem. 2002, 74, 5383-5392.
Kim, T. H.; Jiang, H. H.; Lim, S. M.; Youn, Y. S.; Choi, K. Y.; Lee, S.; Chen, X.; Byun, Y.; Lee, K. C. "Site-Specific PEGylated Exendin-4 Modified with a High Molecular Weight Trimeric PEG Reduces Steric Hindrance and Increases Type 2 Antidiabetic Therapeutic Effects," Bioconjugate Chem. 2012, 23, 2214-2220.
Knudsen, "Glucagon-like Peptide-1: The Basis of a New Class of Treatment for Type 2 Diabetes" J. Med. Chem, 2004, 47: 4128-4134.

Kobashigawa, Yet al. "Attachment of an NMR-Invisible Solubility Enhancement Tag Using a Sortase-Mediated Protein Ligation Method," J Biomol NMR. Mar. 2009, vol. 43, No. 3; pp. 145-150.
Kruger et al., "Analysis of the Substrate Specificity of the Staphylococcus aureus Sortase Transpeptidase SrtA†," Biochemistry, 2004, 43, 1541-1551.
Kyte et al., "A Simple Method for Displaying the Hydropathic Character of a Protein," J. Mol. Biol., 1982, 157, 105-132.
Le Droumaguet, B.; Nicolas, J. "Recent advances in the design of bioconjugates from controlled/living radical polymerization," Polym. Chem. 2010, 1, 563-598.
Lele, B., et al., "Synthesis of Uniform Protein-Polymer Conjugates" Biomacromolecules 2005, 6, 3380-3387.
Leung, M. K. M.; Hagemeyer, C. E.; Johnston, A. P. R.; Gonzales, C.; Kamphuis, M. M. J.; Ardipradja, K.; Such, G. K.; Peter, K.; Caruso, F. "Bio-Click Chemistry: Enzymatic Functionalization of PEGylated Capsules for Targeting Applications**," Angew. Chem. Int. Ed. 2012, 51, 7132-7136.
Lim, et al., "Improved Non-Chromatographic Purification of a Recombinant Protein by Cationic Elastin-like Polypeptides" Biomacromolecules, 2007, 8(5): 1417-1424.
Ling, J.J. et al., "Protein thioester synthesis enabled by sortase," J. Am Chem Soc, 2012, 134(26):10749-10752.
Liu, J.; Bulmus, V.; Herlambang, D. L.; Barner-Kowollik, C.; Stenzel, M. H.; Davis, T. P. "In Situ Formation of Protein-Polymer Conjugates through Reversible Addition Fragmentation Chain Transfer Polymerization**," Angew. Chem. Int. Ed. 2007, 46, 3099-3103.
Magnusson, J. P.; Bersani, S ; Salmaso, S.; Alexander, C.; Caliceti, P. "In Situ Growth of Side-Chain PEG Polymers from Functionalized Human Growth HormonesA New Technique for Preparation of Enhanced Protein-Polymer Conjugates," Bioconjugate Chem. 2010, 21, 671-678.
Mao, H. et al., "Sortase-mediated protein ligation: a new method for protein engineering," J Am Chem Soc, 2004, 126(9):2670-2671.
Maraffini, L.A. et al., "Sortases and the art of anchoring proteins to the envelopes of Gram-positive bacteria," Microbiol Mol Biol Rev, 2006, 70(1):192-221.
McHale et al., "Synthesis and in Vitro Evaluation of Enzymatically Cross-Linked Elastin-Like Polypeptide Gels for Cartilaginous Tissue Repair" Tissue Engineering, 2005, 11: 1768-1779.
Mero, A. et al., "Transglutaminase-mediated PEGylation of proteins: direct identification of the sites protein medification by mass spectrometry using a novel monodisperse PEG," Bioconjug Chem, 2009, 20(2):384-389.
Meyer, D.R. et al., "Purification of recombinant proteins by fusion with thermally-responsive polypeptides," Nat Biotechnol, 1999, 17(11):1112-1115.
Nicolas, J.; San Miguel, V.; Mantovani, G.; Haddleton, D. M. "Fluorescently tagged polymer bioconjugates from protein derived macroinitiators," Chem. Commun. 2006, 45, 4697-4699.
Pace et al., "How to measure and predict the molar absorption coefficient of a protein" Protein Science 1995, 4: 2411-2423.
Popp, M. et al., "Sortase-Catalyzed Transformations That Improve the Properties of Cytokines," PNAS, 2011, vol. 108, No. 8, pp. 3169-3174.
Popp, M. W.; Antos, J. M.; Ploegh, H. L."Sortase-catalyzed transformations that improve the properties of cytokines," Curr. Protoc. Protein Sci. 2009, 56, 15.3.1.
Richards, J. et al., "Engineered fibronectin type III domain with RGDWE sequence binds with enhanced affinity and specificity to human avβ3 integrim," J Mol Biol, 2003, 326(5):1475-1488.
Shen, B.Q. et al., "Conjugation site modulates the in vivo stability and thearpeutic activity of antibody-drug conjugates," Nat Biotechnol, 2012, 30(2):184-189.
Shimoboji, T.; Larenas, E.; Fowler, T.; Hoffman, A. S.; Stayton, P. S. "Temperature-Induced Switching of Enzyme Activity with Smart Polymer-Enzyme Conjugates," Bioconjugate Chem. 2003, 14, 517-525.
Siegwart, D. et al., "ATRP in the Design of Functional Materials for Biomedical Applications," Prog Polymer Science, 2012, vol. 37, No. 1, pp. 18-37.

(56) References Cited

OTHER PUBLICATIONS

Sumerlin, B. S. "Proteins as Initiators of Controlled Radical Polymerization: Grafting-from via ATRP and RAFT," ACS Macro Lett. 2012, 1, 141-145.
Swee, L.K. et al., "Sortase-mediated modification of αDEC205 affords optimization of antigen presentation and immunization against a set of viral epitopes," Proc Natl Acad Sci USA, 2013, 110(4):1428-1433.
Ton-That, H. et al., "Assembly of pili on the surface of Corynebacterium diptheriae," 2003, 50(4):1429-1438.
Ton-That, H. et al., "Purification and characterization of sortase, the transpeptide that cleaves surface proteins of Staphylococcus aureus and the LPXTG motif," Proc Natl Acad Sci USA, 1999, 96(22):12424-12429.
Trabbic-Carlson, K., "Expression and purification of recombinant proteins from *Escherichia coli*: Comparison of an elastin-like polypeptide fusion with an oligohistidine fusion" Protein Science, 2004, 13: 3274-3284.
Williamson, D.J. et al., "Efficient N-terminal labeling of proteins by use of sortase," Angew Chem Int ed Engl, 2012, 51(37):9377-9380.
Wu, P. et al., "Site-specific chemical modification of recombinant proteins produced in mammalian cells by using the genetically encoded aldehyde tag," Proc Natl Acad Sci USA, 2009, 106(9):3000-3005.
Wu, Z.; Guo, X.; Wang, Q.; Swarts, B. M.; Guo, Z. "Sortase A-Catalyzed Transpeptidation of Glycosylphosphatidylinositol Derivatives for Chemoenzymatic Synthesis of GPI-Anchored Proteins," J. Am. Chem. Soc. 2010, 132, 1567-1571.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
PCT/US2010/024385 International Preliminary Report on Patentability and Written Opinion dated May 5, 2010 (7 pages).
PCT/US2010/024385 International Search Report dated May 5, 2010 (2 pages).
United States Patent Office Action for U.S. Appl. No. 13/201,502 dated Jan. 15, 2013 (14 pages).
United States Patent Office Notice of Allowance for U.S. Appl. No. 13/201,502 dated Apr. 30, 2013 (11 pages).
International Search Report and Written Opinion for Application No. PCT/US14/40319 dated Oct. 10, 2014 (15 pages).
PCT/US2015/017601 International Search Report and Written Opinion dated Aug. 18, 2015 (19 pages).

ENZYME-CATALYZED SYNTHESIS OF SITE-SPECIFIC AND STOICHIOMETRIC BIOMOLECULE-POLYMER CONJUGATES

CROSS-REFERENCE TO RELATED APPLICATIONS

This application is a national stage filing under 35 U.S.C. 371 of International Patent Application No. PCT/US2014/040319, filed May 30, 2014, which claims the benefit of priority to U.S. Provisional Patent Application No. 61/828,873, filed May 30, 2013, which are incorporated herein by reference in their entireties.

SEQUENCE LISTING

The sequence listing is filed with the application in electronic format only and is incorporated by reference herein. The sequence listing text file "028193-9161-WO00 As Filed Sequence Listing—Text Version.txt" was created on Jul. 23, 2014, and is 8.874 bytes in size.

STATEMENT REGARDING FEDERALLY SPONSORED RESEARCH

This invention was made with government support under grant R01 GM061232 awarded by the United States National Institutes of Health, grant 5T32 GM008487 awarded by the United States National Institutes of Health, grant R01 GM061232 awarded by the United States National Institutes of Health, and grant R01 A146611 awarded by the United States National Institutes of Health. The government has certain rights in the invention.

BACKGROUND

Proteins and peptides are becoming an important class of therapeutic agents. Despite their high biological activity and specificity, their therapeutic efficacy when delivered in native form is largely hindered by numerous limitations, including short circulation half-life, poor stability, low solubility and immunogenicity. Frequent administration of the agent may be required, which may increase cost, inconvenience and the risk of adverse reactions.

Conjugating biomolecules with stealth polymers has become a commonly used method to address these limitations. Polypeptide-polymer conjugates are conventionally synthesized using the "grafting to" method, in which the polymer is first pre-synthesized, and then conjugated to the polypeptide post-polymerizationally. Such an approach typically results in poor yield due to steric hindrance between the biomolecule and polymer and difficulty in product purification as a result of similar sizes and surface properties of the reactants and products. Additionally, conjugation is often done in a non-specific manner, by exploiting promiscuously distributed reactive side chains or residues that are only partially solvent accessible. As a result, large degree of heterogeneity is often found in the product, significantly compromising bioactivity.

SUMMARY

Methods are provided of increasing the half-life of polypeptides, such as therapeutic polypeptides, by forming conjugates containing a polymer and a polypeptide. In one aspect, the methods may increase the half-life of a plurality of polypeptides having a polymer attached at the N- or C-terminus. In some embodiments, the polypeptides are contacted with an initiator agent and an enzyme such as a sortase under conditions that permit attachment of the initiator agent to at least one of the N-terminus and the C-terminus of the polypeptides, and are incubated with a monomer under conditions that permit polymerization to occur from the initiator agent to form polypeptide-polymer conjugates. In some embodiments, polymerization may occur such that at least about 25% of the polypeptides have a conjugated polymer initiated from at least one of the N-terminus and the C-terminus, the polypeptide-polymer conjugates have an in vivo half-life that is at least 50% greater than the in vivo half-life of the polypeptides or a combination thereof.

In some embodiments, methods of making polypeptide-polymer conjugates having one or more altered pharmacological properties from a plurality of polypeptides having C-termini are provided. A plurality of polypeptides are contacted with a sortase and an initiator agent under conditions that permit attachment of the initiator agent to the C-terminus and are incubated with a monomer under conditions that permit free-radical polymerization to occur from the initiator agent to form polypeptide-polymer conjugates. In some embodiments, polymerization may occur such that at least about 25% of the polypeptides have a conjugated polymer initiated solely from the C-terminus, and the polypeptide-polymer conjugates have an altered pharmacological property such as an increased in vivo half-life or an in vivo biodistribution to a tissue, organ or disease site that is greater than the in vivo biodistribution of the plurality of polypeptides. In some embodiments, the methods yield, for example, at least 50%, 75% or 85% polymer-polypeptide conjugates having a polymer solely attached at the C-terminus, calculated as a proportion of the total polymer-polypeptide conjugates and unreacted macroinitiators that are separated following the polymerization reaction.

Other aspects of the invention will become apparent by consideration of the detailed description and accompanying drawings.

DETAILED DESCRIPTION

Figure 1:
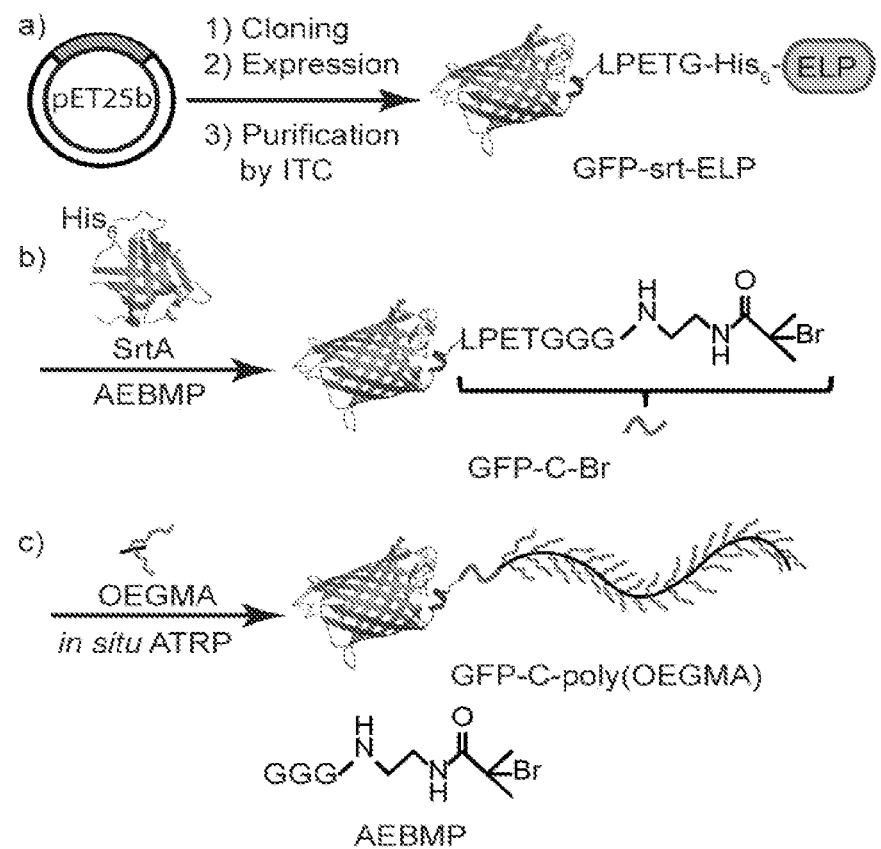
FIG. 1: Synthetic route of GFP-C-poly(OEGMA). a) Recombinant expression of ternary fusion protein GFP-srt-ELP and purification by inverse transition cycling (ITC). b) SrtA-catalyzed site-specific attachment of the ATRP initiator AEBMP to the C-terminus of GFP. c) In situ ATRP of OEGMA yielding GFP-C-poly(OEGMA).

Polypeptide-polymer conjugates may be formed by attaching preformed polymers with reactive end groups to targets on the polypeptides via a variety of coupling reactions. For example, conjugation of therapeutic proteins with polymers such as polyethylene glycol, can prolong the serum half-life and reduce immunogenicity of the proteins. However, the stability and properties of these conjugates may be insufficient and difficult to predict, because the type and frequency of attachment of the preformed polymer may be difficult to control.

"Grafting from" techniques, or growing polymers directly from biomolecular macroinitiators, permits more defined linkages between the polypeptide and synthesized polymer chain. Described herein is a technology which utilizes an enzyme to achieve site-specific attachment of a polymerization initiator solely at the terminus of a protein, for example the C-terminus to form a macroinitiator, allowing for subsequent in situ growth of a stealth polymer from the macroinitiator. The methods suitably yield site-specific (e.g. C-terminal) and stoichiometric (one polymer chain per protein subunit) conjugates. The enzyme-catalyzed initiator attachment reaction can proceed with specificity, near quantitative conversion and little or no side product. In situ grafting of polymer from the macroinitiator can produce conjugates with high yield and low dispersity. Both initiator attachment and polymer grafting can be carried out in mild aqueous conditions which do not cause denaturation of the protein. Because the product is much larger than the reagents, the synthesized conjugates can be purified in a single step, such as by a single run of Size Exclusion Chromatography. Other purification techniques may be used including, without limitation, ion exchange chromatography, hydrophobic interaction chromatography, immobilized metal affinity chromatography (for example if a His-tag is present, for example, on the N-terminus of the polypeptide), range of affinity chromatography (for example if an affinity tag is present on, for example, the N-terminus of the polypeptide), dialysis, filtration and ultracentrifugation using, for example, a membrane or centrifugal filter unit with a suitable molecular weight cutoff. An overall yield of at least about 50%, at least about 55%, at least about 60%, at least about 65%, at least about 70%, at least about 75%, at least about 80%, at least about 85%, or at least about 90% can be achieved. As the C-terminus is conserved on proteins and peptides, the methods described herein provide a strategy for synthesizing site-specific and stoichiometric biomolecule-polymer conjugates with high yield.

Enzymes suitable for C-terminal attachment of an initiator include sortases. Sortases are transpeptidases synthesized by prokaryotic organisms which modify proteins by recognizing and cleaving a carboxyl-terminal sorting signal. N-terminal modification can also be achieved with Sortases, typically at a lower efficiency than the C-terminal mechanism. The most common substrates recognized by sortase enzymes contain the motif LPXTG (Leu-Pro-any-Thr-Gly) (SEQ ID NO: 3), where X is any amino acid, followed by a hydrophobic transmembrane sequence and a cluster of basic residues, such as arginine. Cleavage occurs between the Thr and Gly, with transient attachment of the Thr residue to the active site Cys residue on the enzyme, followed by nucleophilic substitution of the enzyme to complete transpeptidation. Sortases include Sortase A, Sortase B, Sortase C and Sortase D. These four main types can be found distributed in various strains of gram-positive bacteria. Other Sortases include mutant sortases produced through directed evolution which are able to recognize alternative substrates not typically recognized in nature. Sortases recognizing alternative substrates may be used to meet different application needs.

Sortase A catalyzes the cleavage of the LPXTG (SEQ ID NO: 3) motif on a target protein with the concomitant formation of an amide linkage between a nucleophile, for example an oligoglycine peptide, and the cleaved target protein. Suitably, the enzyme is recombinantly expressed and purified for use in the methods described herein. Sortase A recognizes the pentapeptide sequence "LPXTG" (SEQ ID NO: 3; where "X" is any standard amino acid residue) embedded in or terminally attached to a protein or peptide, and its Cys nucleophilically attacks the amide bond between Thr and Gly within the recognition sequence, generating a relatively long-lived enzyme-thioacyl intermediate. To complete transpeptidation, a second (bio)molecule with an N-terminal nucleophilic group, typically an oligoglycine motif, attacks the intermediate, displacing Sortase A and joining the two molecules via a native peptide bond.

As shown in FIG. 1a, a ternary fusion protein, such as "GFP-srt-ELP", can be recombinantly expressed to serve as the sortase substrate. In FIG. 1, "srt" stands for the native SrtA recognition sequence "LPETG" (SEQ ID NO: 2), and ELP (SEQ ID NO: 4) refers to an environmentally responsive elastin-like polypeptide (ELP) that facilitates easy purification of the ternary fusion by inverse transition cycling (ITC), a non-chromatographic protein purification method, and SrtA refers to Sortase A (SEQ ID NO: 5 or 6, encoded by SEQ ID NO: 11 or 12, respectively). Purification can also be achieved for example, with a His$_6$-tag using immobilized metal affinity chromatography (IMAC). The polypeptide-polymer conjugates can also be purified by other chromatographic methods which may or may not exploit a tag or purification moiety, such as size exclusion chromatography (SEC), ion exchange chromatography (IEC), and hydrophobic interaction chromatography (HIC). When ELP (SEQ ID NO: 4) is used, the recognition sequence can be located between the protein and the ELP (SEQ ID NO: 4), so that transpeptidation by Sortase A (SEQ ID NO: 5 or 6, encoded by SEQ ID NO: 11 or 12, respectively) not only attaches the initiator to green fluorescent protein (GFP; SEQ ID NO: 7) but also conveniently liberates the purification tag. As transpeptidation relies on the presence of the enzyme, cleavage does not begin until Sortase A is added in vitro. Very little, if any, of the protein is thus lost in vivo before purification, hence increasing the overall product yield.

In some embodiments the methods yield a polypeptide which has a single polymer attached at the terminus such as the C terminus or the N terminus. Polypeptides having a polymer attached solely at the terminus, such as the C terminus, may constitute at least about 50%, at least about 55%, at least about 60%, at least about 65%, at least about 70%, at least about 75%, at least about 80%, at least about 85%, at least about 90% or at least about 95% of the total polypeptides used in the methods and contacted with the enzyme and initiator.

Yield of polypeptide-polymer conjugates can be high. For example, the amount of polypeptides having a single polymer attached at the terminus following polymerization as a proportion of the total amount of conjugated and unconjugated polypeptides recovered following polymerization can be at least about 50%, at least about 55%, at least about 60%, at least about 65%, at least about 70%, at least about 75%, at least about 80%, at least about 85%, at least about 90%, or at least about 95%. Following the polymerization reaction, the conjugated and unconjugated polypeptides can be separated and the conjugates recovered by chromatography, differential centrifugation or ultrafiltration, and the amount of conjugated polypeptides relative to the total amount of conjugated and unconjugated polypeptides can be calculated. For example, a chromatograph with peaks corresponding to the conjugates having a single polymer attached and remaining unreacted polypeptide macroinitiator can be used to calculate the yield efficiency.

Figure 2:
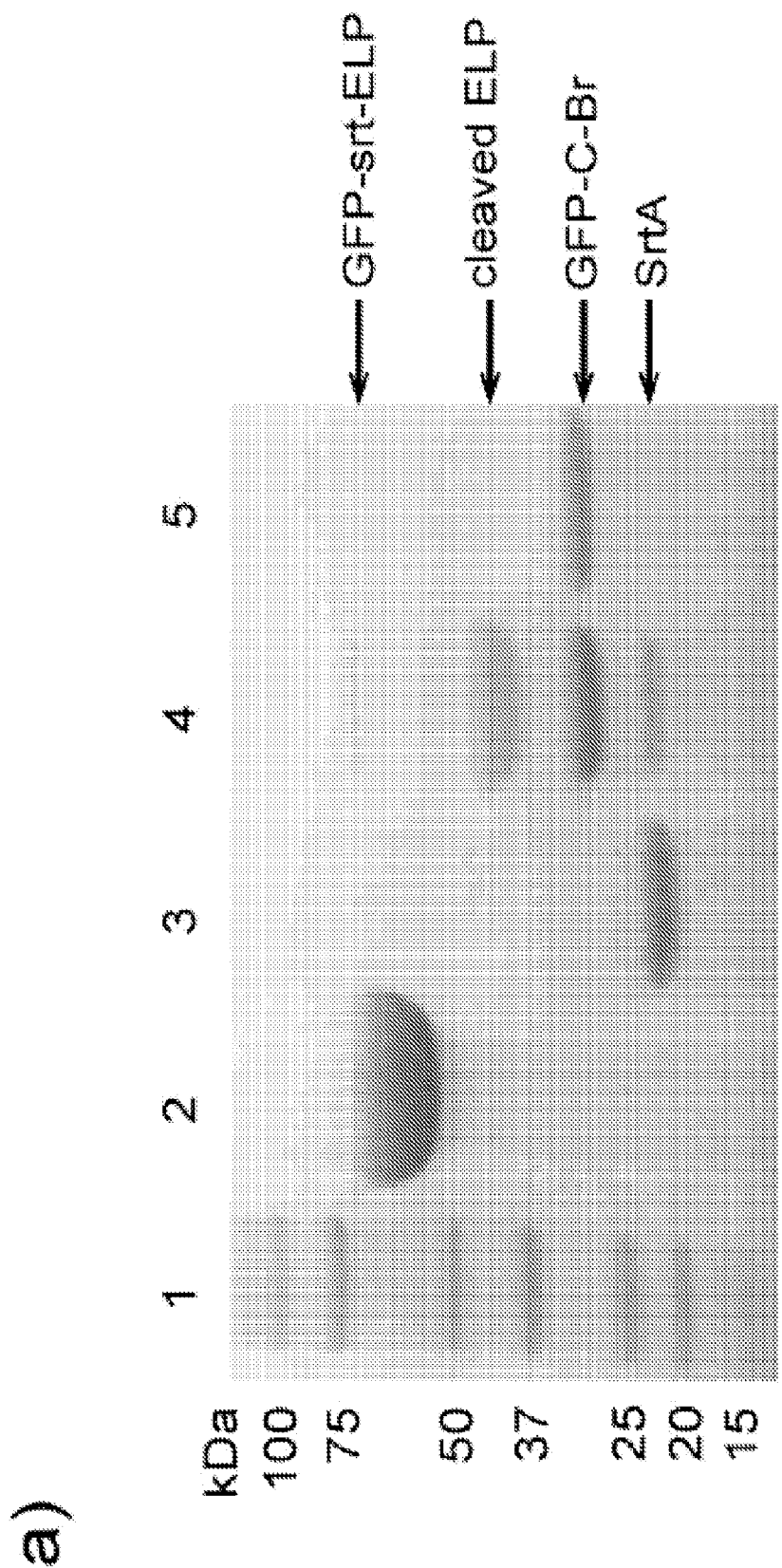
FIG. 2: a) Photograph showing an SDS-PAGE analysis of initiator attachment by SrtA. Lane 1: MW marker, lane 2: GFP-srt-ELP, lane 3: SrtA, lane 4: sortase-catalyzed initiator attachment (SCIA) reaction mixture after 5 h of reaction, lane 5: purified GFP-C macroinitiator. b) Graph depicting isotopic distribution of GFP-C-Br C-terminal peptide [DH-MVLLEFVTAAGITHGMDELYNVDGGGSLPET-"AEBMP"]$^{3+}$ (DHMVLLEFVTAAGITHGMDELYN-VDGGGSLPET is SEQ ID NO: 1) detected by LC/MS-MS after trypsin digestion. c) Graph depicting SEC traces of GFP-C-Br (rightmost peak), and three ATRP reaction (Rxn) attempts, Rxn 1 (center-right peak), Rxn 2 (center-left peak), and Rxn 3 (leftmost peak) detected by UV absorbance at 280 nm.
Figure 2:
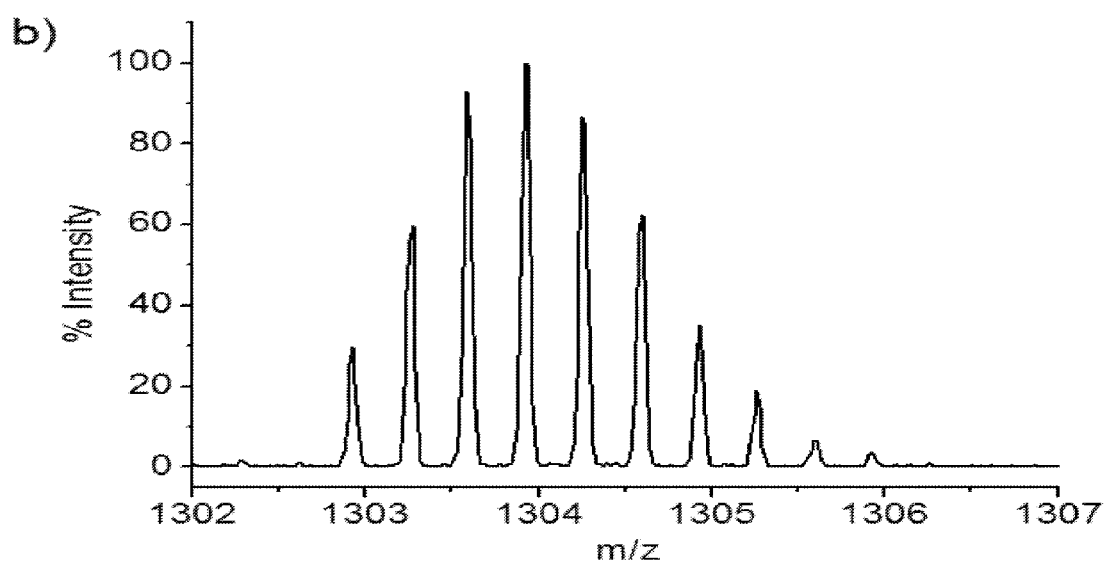
Figure 2:
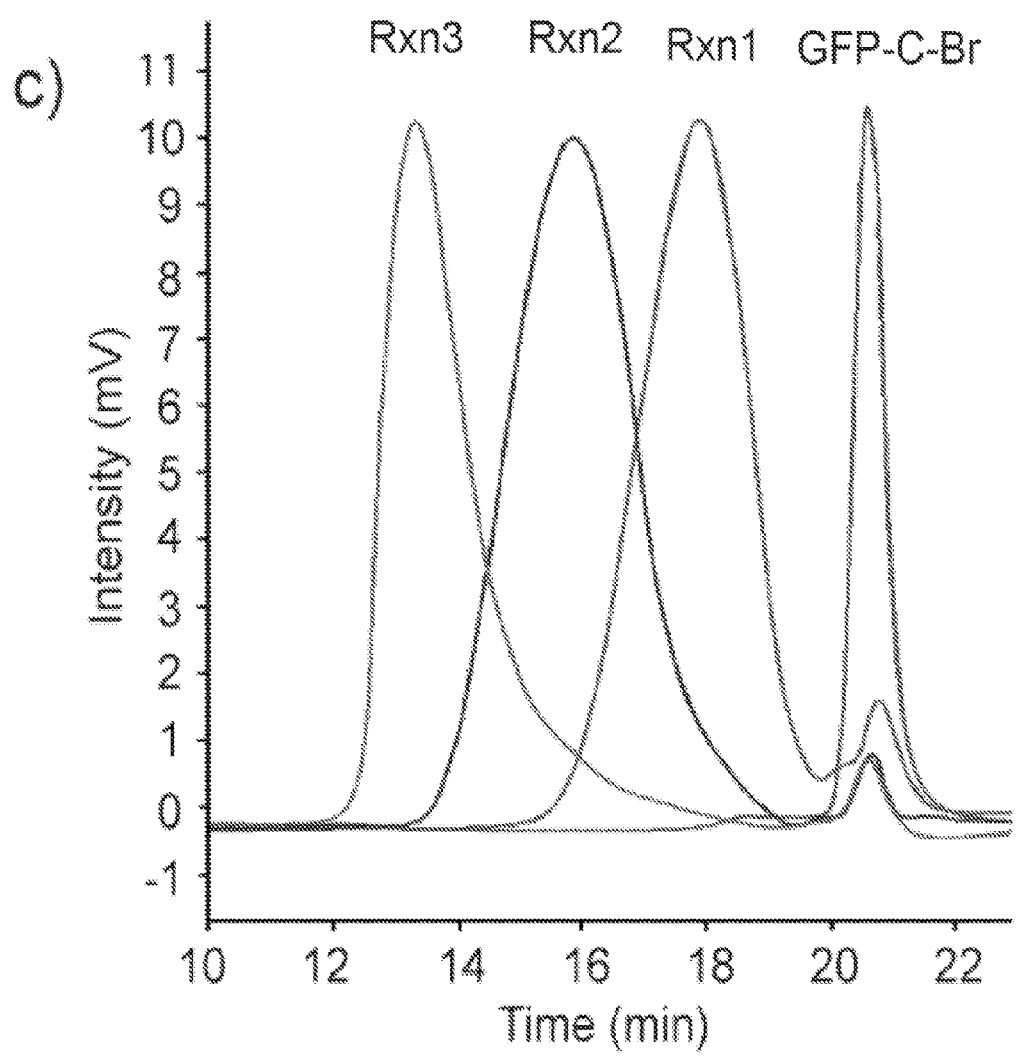
Figure 7:
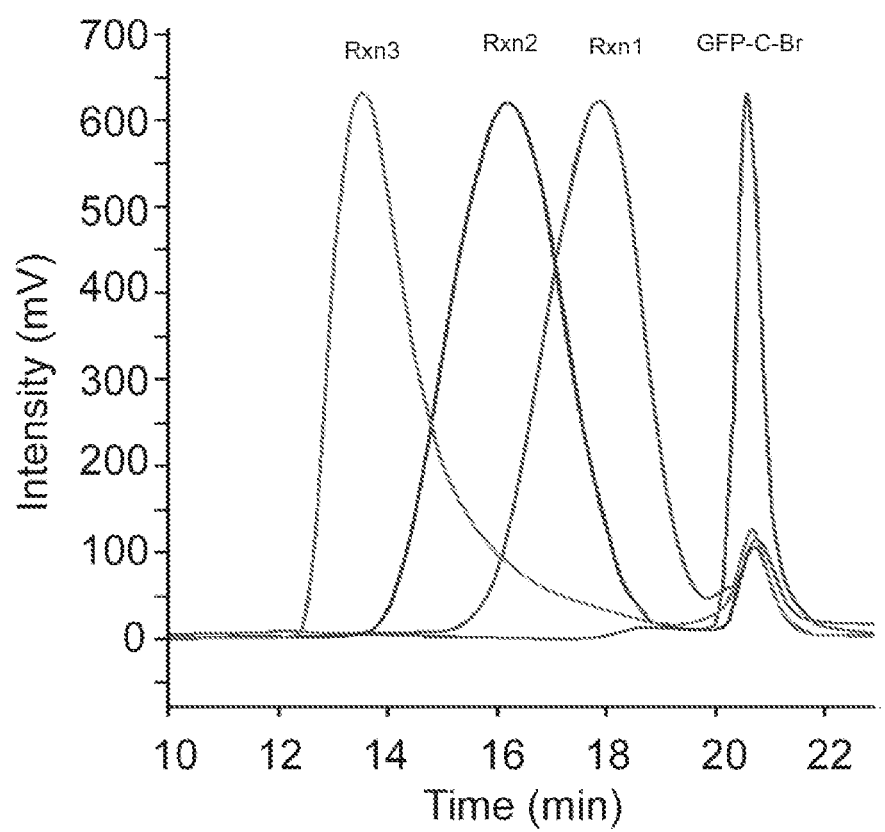
FIG. 7: Graphs depicting SEC traces of GFP-C-Br (rightmost peak), and conjugates from Rxn 1 (center-right peak), Rxn 2 (center-left peak), Rxn 3 (leftmost peak) detected by fluorescence at 460 nm excitation and 507 nm emission.

To determine conjugation efficiency of in situ polymerization such as ATRP from the C-terminus of a polypeptide, for example, GFP (SEQ ID NO: 7), reaction mixtures can be analyzed by chromatography, such as Size Exclusion Chromatography (SEC) using either or both UV detection at 280 nm and fluorescence detection. Exemplary chromatograms of three such reactions (left-most peaks) are shown in FIG. 2 and FIG. 7, where in each chromatogram, the earlier eluting peak corresponds to the GFP-C-poly(OEGMA) conjugates and the later eluting peak around 21 min corresponds to GFP-C-Br. Area under the curve (AUC) can be used to calculate the conjugate and unreacted protein peaks. For example, the AUC of the GFP-C-poly(OEGMA) conjugate peak and the residual unreacted GFP-C-Br macroinitiator peak in the chromatogram of each polymerization reaction mixture can be computed using software known in the art, such as EZStart software (v. 7.4, Shimadzu). Sum of the areas of the two peaks in each chromatogram can be regarded as 100% and the percent fraction of the conjugate peak can be recorded as the conjugation efficiency of that particular polymerization reaction. Values from repeated reactions can be used to calculate the mean and standard deviation of conjugation efficiency. For example, a calculation for chromatograms detected by UV-vis absorbance is shown in Table 3 and for fluorescence in Table 4.

Methods are provided for synthesizing polypeptide-polymer conjugates, in which the polymer is formed in situ on the polypeptide, such as at the C-terminus of the polypeptide. The polypeptide-polymer conjugates show an increased half-life in vivo or in serum, or other desirable pharmacological properties, compared with polypeptides that have not had polymers formed in situ according to methods described herein. The methods facilitate growth of polymers that can be regulated and controlled to produce a conjugate having particular desired features.

Methods for synthesizing polypeptide-polymer conjugates are also provided in which a polymer is synthesized in situ from a terminus of the polypeptide using an enzyme such as a sortase. The C-terminus of the polypeptide, for example, is modified with an initiator agent that facilitates polymerization from the C-terminus. The attachment of an initiator using an enzyme such as a sortase has the advantage that there is no requirement for fusion to a relatively large domain, such as an intein domain, that can, in some instances, reduce the expression of the fusion protein.

The polypeptide-polymer conjugates comprise a polypeptide to which a polymer is attached at the C-terminus of the polypeptide. In one embodiment, only one polymer is attached per polypeptide. Examples of polypeptides include, but are not limited to, proteins, and peptide sequences, such as, without limitation, peptide sequences comprising at least about 5 amino acids, at least about 10 amino acids, at least about 20 amino acids, at least about 30 amino acids, at least about 40 amino acids, at least about 50 amino acids, at least about 75 amino acids, at least about 100 amino acids, at least about 150 amino acids, at least about 200 amino acids, at least about 250 amino acids, at least about 300 amino acids, at least about 400 amino acids, at least about 500 amino acids, at least about 600 amino acids, at least about 700 amino acids, at least about 800 amino acids, at least about 900 amino acids, or at least about 1000 amino acids, or more. Examples of proteins and polypeptides include any natural or synthetic polypeptide that may be administered to a patient.

Examples of polypeptides include, but are not limited to, those of interest in medicine, agriculture and other scientific and industrial fields, particularly including therapeutic polypeptides such as interferons, insulin, monoclonal antibodies, blood factors, colony stimulating factors, growth hormones, interleukins, growth factors, therapeutic vaccines, calcitonins, tumor necrosis factors (TNF), and enzymes. Specific examples of such therapeutic proteins include, without limitation, enzymes utilized in enzyme replacement therapy; hormones for promoting growth in animals, or cell growth in cell culture; anticoagulants and active proteinaceous substances used in various applications, for example, in biotechnology or in medical diagnostics. Specific examples include, but are not limited to: asparaginase; glutamase; arginase; arginine deaminase; adenosine deaminase ribonuclease; cytosine deaminase, trypsin; chymotrypsin, papin, epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons;

interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; luteinizing hormone-releasing hormone (LHRH); growth hormone-releasing hormone (GHRH); tissue plasminogen activators; interleukin-1; interleukin-15; interleukin-2, interleukin-10, GMCSF, GCSF, betatrophin, interleukin-1 receptor antagonist (IL-1RA); glucagon-like peptide-1 (GLP-1); TNF-related apoptosis-inducing ligand (TRAIL), glucagon-like peptide-1 (GLP-1), vasoactive intestinal peptide (VIP), betatrophin, exenatide, leptin, ghrelin; granulocyte monocyte colony stimulating factor (GM-CSF); interleukin-2 (IL-2); interferons such as interferon-α; interferon-gamma, adenosine deaminase; cytosine deaminase, uricase; asparaginase; human growth hormone; asparaginase; macrophage activator; chorionic gonadotropin; heparin; atrial natriuretic peptide; hemoglobin; retroviral vectors; relaxin; cyclosporin; oxytocin; vaccines; monoclonal antibodies; single chain antibodies, ankyrin repeat proteins, affibodies, and the like; and analogs and derivatives thereof.

The polymer that is grown in situ from the polypeptide confers desirable properties to the conjugate. The term "polymer" as used herein is intended to encompass a homopolymer, heteropolymer, block polymer, co-polymer, ter-polymer, etc., and blends, combinations and mixtures thereof. Examples of polymers include, but are not limited to, functionalized polymers, such as a polymer comprising 5-vinyltetrazole monomer units and having a molecular weight distribution less than 2.0. The polymer may be or contain one or more of a star block copolymer, a linear polymer, a branched polymer, a hyperbranched polymer, a dendritic polymer, a comb polymer, a graft polymer, a brush polymer, a bottle-brush copolymer and a crosslinked structure, such as a block copolymer comprising a block of 5-vinyltetrazole monomer units. Such a block copolymer may further be capable of selective separation of closely related chemical species such as ions, proteins or nucleic acids via ionic bonding or complex formation.

Polymers that can be produced in situ on the polypeptide according to the methods disclosed herein include, without limitation, polyesters, poly(meth)acrylamides, poly(meth) acrylates, polyethers, polystyrenes, polynorbornenes and monomers that have unsaturated bonds. For example, amphiphilic comb polymers are described in U.S. Patent Application Publication No. 2007/0087114 and in U.S. Pat. No. 6,207,749 to Mayes et al., the disclosure of each of which is herein incorporated by reference in its entirety. The amphiphilic comb-type polymers may be present in the form of copolymers, containing a backbone formed of a hydrophobic, water-insoluble polymer and side chains formed of short, hydrophilic non-cell binding polymers. Examples of other polymers include, but are not limited to, polyalkylenes such as polyethylene and polypropylene; polychloroprene; polyvinyl ethers; such as poly(vinyl acetate); polyvinyl halides such as poly(vinyl chloride); polysiloxanes; polystyrenes; polyurethanes; polyacrylates; such as poly(methyl (meth)acrylate), poly(ethyl (meth)acrylate), poly(n-butyl (meth)acrylate), poly(isobutyl(meth)acrylate), poly(tert-butyl (meth)acrylate), poly(hexyl(meth)acrylate), poly (isodecyl(meth)acrylate), poly(lauryl (meth)acrylate), poly (phenyl (meth)acrylate), poly(methyl acrylate), poly (isopropyl acrylate), poly(isobutyl acrylate), and poly (octadecyl acrylate); polyacrylamides such as poly (acrylamide), poly(methacrylamide), poly(ethyl acrylamide), poly(ethyl methacrylamide), poly(N-isopropyl acrylamide), poly(n, iso, and tert-butyl acrylamide); and copolymers and mixtures thereof. These polymers may include useful derivatives, including polymers having substitutions, additions of chemical groups, for example, alkyl groups, alkylene groups, hydroxylations, oxidations, and other modifications routinely made by those skilled in the art. The polymers may have side chains of betaine, carboxybetaine, sulfobetaine, oligoethylene glycol (OEG), sarcosine or polyethyleneglycol (PEG). For example, poly(oligoethyleneglycol methacrylate) (poly(OEGMA)) may be used in methods of the invention to produce polypeptide-p-OEGMA or biomolecule-poly(OEGMA) conjugates. Poly(OEGMA) may be hydrophilic, water-soluble, non-fouling, non-toxic and non-immunogenic due to the OEG side chains, such that conjugating proteins or polypeptides at the N- and/or C-termini with poly(OEGMA) can improve protein stability, pharmacokinetics and immunogenicity.

The polypeptide-polymer conjugates may be formed by contacting the polypeptide with an initiator and one or more monomers under conditions that permit polymerization to occur. To form the polymer in situ and produce a conjugate, the polypeptide may be contacted with an initiator agent and an enzyme, such as a sortase, under conditions that permit attachment of the initiator agent to the polypeptide. The initiator attaches to the polypeptide, for example, to the end of the polypeptide, such as at one or more of the N-terminus or C-terminus of a polypeptide, protein or combination thereof. The polypeptide and initiator may be contacted subsequently or at least partially simultaneously with a monomer under conditions suitable for polymerization to occur. Accordingly, initiation sites on the polypeptide can be generated prior to polymerization, or concurrently as polymerization occurs. Polymerization may include, for example, atom transfer radical polymerization (ATRP), reversible addition-fragmentation chain transfer (RAFT) polymerization, nitroxide mediated radical polymerization (NMP), ring-opening metathesis polymerization (ROMP), and combinations thereof.

The methods may permit precise design of polypeptide-polymer conjugates or protein-polymer conjugates and may provide advantages that include a reduction or elimination of postpolymerization modification strategies and polypeptide-polymer or protein-polymer coupling reactions, and simplification of the purification of the final bioconjugate from monomer, polymer and/or catalyst. The methods may permit attachment of polymers to polypeptides in a sample such that at least about 10%, at least about 20%, at least about 30%, at least about 40%, at least about 50%, at least about 60%, at least about 70%, at least about 80%, at least about 90%, or at least about 95% of the polypeptides or biomolecules in the sample have one polymer attached per biomolecule. The methods may permit attachment of polymers to the terminus, such as the C-terminus, of polypeptides in a sample such that at least about 10%, at least about 20%, at least about 30%, at least about 40%, at least about 50%, at least about 60%, at least about 70%, at least about 80%, at least about 90%, or at least about 95% of the polypeptides or biomolecules in the sample have one polymer attached at the C-terminus per biomolecule.

Stoichiometric attachment of one, two, three, four, five, six, seven, eight, nine, or ten or more polymers per biomolecule such that at least about 10%, at least about 20%, at least about 30%, at least about 40%, at least about 50%, at least about 60%, at least about 70%, at least about 80%, at least about 90%, or at least about 95% of biomolecules in the sample have the particular desired number of polymers attached is also permitted.

The methods may permit attachment of polymers to polypeptides in a sample such that at least about 10%, at least about 20%, at least about 30%, at least about 40%, at least about 50%, at least about 60%, at least about 70%, at least about 80%, at least about 90%, or at least about 95% of the polypeptides have a conjugated polymer initiated from at least one end of the biomolecule, or from solely one end of the polypeptide, such as the C-terminus or the N-terminus. The polypeptide-polymer conjugates may be substantially free of attachment of polymers at sites within the biomolecule. The polypeptide-polymer conjugates may be substantially free of attachment of polypeptides throughout the polymers.

For example, the methods may permit attachment of polymers to polypeptides in a sample such that at least about 10%, at least about 20%, at least about 30%, at least about 40%, at least about 50%, at least about 60%, at least about 70%, at least about 80%, at least about 90%, or at least about 95% of the polypeptides have a polymer attached solely or only to the C-terminus, solely or only to the N-terminus, or solely or only to both the N and C-termini. The polypeptide-polymer conjugates may be substantially free of attachment of polymers at sites within the polypeptide. The polypeptide-polymer conjugates may be substantially free of attachment of polypeptides throughout the polymers.

A variety of monomers may be suited for use in methods of the invention. Exemplary monomers include, but are not limited to, lactic acid, epichlorohydrin, acrylate, methacylate, acrylamide, methacrylamide, norbornene, and oxanorbornene. Examples of monomer structures that may be used in ROMP, NMP, ATRP and RAFT, and other components and techniques that may be used are described in U.S. Patent Publication No. 20110294189, the entire disclosure of which is herein incorporated by reference in its entirety.

The monomer may be, for example, non-biodegradable and/or hydrophobic. The monomer may include two reactive groups, both of which are reacted in order to form the polymer. For example, lactic acid includes two reactive groups, a hydroxy group and a carboxy group.

Monomers which contain one or more additional reactive groups may be incorporated into the polymer backbone. For example, a reactive monomer may be incorporated in the growing polymer chain by participating in the same types of chemical reactions as the growing polymer chain. For example, when lactide is being polymerized using a Lewis acid catalyst, a depsipeptide (cyclic dimer of an amino acid) can be prepared from lysine, in which the epsilon amine group is protected, for example, with a t-boc protecting group. The lysine is incorporated into the polymer, and the protecting group can be removed. The resulting amine groups are reactive with hydrophilic polymers which include leaving groups such as tosylates, tresylates, mesylates, triflates and other leaving groups well known to those of skill in the art.

Alternatively, the reactive monomer can include a leaving group that can be displaced with a nucleophilic group on a hydrophilic polymer. For example, epichlorohydrin can be used during the polymerization step. The monomer is incorporated into the polymer backbone, and the chloride group is present on the backbone for subsequent reaction with nucleophiles. An example of a hydrophilic polymer containing a nucleophilic group is a PEG with a terminal amine group. PEG-NH$_2$ can react with the chloride groups on the polymer backbone to provide a desired density of PEGylation on the polymer backbone. Using the chemistry described herein, along with the general knowledge of those of skill in the art, one can prepare polymer backbones, which include suitable leaving groups or nucleophiles for subsequent coupling reactions with functionalized hydrophilic polymers.

Polymers may be polymerized in situ on the biomolecule or polypeptide at an initiation site using an initiator agent. An initiator agent is a molecule that assists in beginning the polymerization by interacting with the biomolecule and the monomer. Examples of initiator agents include those compatible with ATRP such as, without limitation, N-(2-aminoethyl)-2-bromo-2-methylpropanamide, N-(2-aminoethyl)-2-chloro-2-methylpropanamide, 2-bromo-N-(2-(2-hydrazinylacetamido) ethyl)-2-methylpropanamide, 2-chloro-N-(2-(2-hydrazinylacetamido) ethyl)-2-methylpropanamide. Examples of initiator agents and systems also include those compatible with RAFT such as, without limitation, a chain transfer agent (CTA), ZC(=S)SR, where R can be cysteine, hydrazine, hydroxylamine, and Z can be phenyl, alkyl, phthalimidomethyl, coupled with traditional radical polymerization initiators including those such as AIBN which are cleaved to initiate the polymerization. Examples of initiators also include those compatible with ROMP such as, without limitation, A-B, where A can be cysteine, hydrazine, hydroxylamine, and B can be olefins.

The methods may produce protein-polymer or polypeptide-polymer conjugates formed through site-specific modifications of the N-terminus or C-terminus of proteins or polypeptides with initiators such as ATRP initiators or RAFT agents, followed by in situ ATRP and RAFT polymerization from the initiators. The approach of modifying proteins with polymers using the N- or C-terminus facilitates attachment of the polymer in a defined manner because each protein usually has an N-terminus and a C-terminus.

In a protein or polypeptide, targets for conjugation and polymerization may include side-chains of natural amino acid (such as lysine and cysteine) and non-canonical amino acid (such as N6-levulinyl lysine and para-azidophenylalanine) on the surfaces of proteins and specific interaction sites in proteins (such as streptavidin and avidin). Particular amino acids, such as the amine side-chain of lysine and the sulfhydryl group of cysteine may be targeted to synthesize protein-polymer conjugates via the "grafting from proteins" method. However, if a protein contains multiple lysines and cysteines on their surfaces this may lead to random modifications at multiple sites on the proteins, resulting in ill-defined biomolecule-polymer conjugates.

Polymerization may be facilitated by the inclusion of a catalyst solution. For example, ATRP catalyst system may include, but are not limited to, copper halides and ligands, where ligands can be derivatives of 2,2'-bipyridine, other π-accepting, chelating nitrogen-based ligands such as 2-iminopyridines and some aliphatic polyamines. RAFT catalyst system may include water soluble radical generating compounds, such as 4,4'-azobis(4-cyanopentanoic acid), 2,2'-Azobis[2-(2-imidazolin-2-yl)propane]dihydrochloride, 2,2'-Azobis[2-(2-imidazolin-2-yl)propane]-disulfate dehydrate, 2,2'-Azobis(2-ethylpropionamidine)-dihydrochloride.

ROMP catalyst systems may include, but are not limited to, soluble Grubbs catalysts, such as tetraethylene glycol substituted ruthenium benzylidene, ruthenium alkylidene with friaryl phosphate ligands, or ruthenium alkylidene with ligands with quaternary ammonium. Other conditions used for polymerization may include, for example, that the polymerization be carried out under low oxygen, for example, under a noble or non-reactive gas such as argon, and/or for a time of at least about 5 min, at least about 15 min, at least about 60 min, and optionally no more than about 12 hr, no more than about 24 hr, no more than about 48 hr. Polymerization may be carried out, for example, at a temperature of at least about 5° C., at least about 10° C., at least about 15° C., at least about 20° C., at least about 30° C., at least about 40° C., at least about 50° C., at least about 60° C., at least about 70° C., at least about 80° C., at least about 90° C. or at least about 100° C.

If desired, biodegradable regions may be introduced into the conjugates, constructed from monomers, oligomers or polymers using linkages susceptible to biodegradation, such as, for example, ester, peptide, anhydride, orthoester, and phosphoester bonds.

The biomolecule-polymer conjugates and polypeptide-polymer conjugates may be used in a number of different applications. For example, they may be used in prolonging the circulation of protein and peptide therapeutic agents in applications that include blood substitutes and targeting solid tumors. For example, they may be used as therapeutic agents, imaging agents, in proteomics, as protective coatings, in composite or smart materials, in sensors, and in the separation or purification of biomolecules, or for preconcentration or preprocessing of samples for assays of other diagnostic devices. Biomolecule-polymer conjugates made as described herein also may be useful in the treatment of diseases and conditions, including, for example, rheumatoid arthritis, Gaucher's disease, hyperuricemia, cancers, solid tumors, diabetes, Alzheimer's disease, hairy cell leukemia, multiple myeloma, venereal warts, AIDS-related Kaposi's sarcoma, chronic hepatitis B and C, inflammatory diseases, autoimmune diseases, infectious diseases and haemostatic disorders.

When used therapeutically, the biomolecule-polymer conjugates and polypeptide-polymer conjugates may have properties that result in improved targeted delivery of biomolecules to disease sites and may thus provide enhanced diagnostic and therapeutic efficacy of these compounds.

The biomolecule-polymer conjugates exhibit desirable properties over non-conjugated biomolecules, polypeptides and proteins, or over polymer conjugates formed using methods other than those described herein. For example, biomolecule-polymer conjugates produced as described herein may show improvement in one or more of solubility, stability, pharmacokinetics, immunogenicity and biodistribution or bioaccumulation at the cell, tissue, disease site, or organ level. The improved stability of the conjugates may manifest as an improvement in the half-life compared with a comparable biomolecule that is not conjugated to a polymer.

The in vivo or serum half-life may be improved. In pharmacokinetics, the half-life is calculated using a start point when the administered pharmaceutical reaches equilibrium following administration. The half-life is the time period in which the pharmaceutical decreases to half the value at equilibrium. The distribution half-life is the period where the decrease occurs due to distribution of the pharmaceutical to the tissue reservoirs, and is typically a steeper curve. The elimination half-life is the period where the decrease occurs due to metabolism and elimination of the pharmaceutical. An area-under the curve analysis can be used to determine the in vivo half-life accounting for the decrease from both distribution and elimination.

The improved half-life (in vivo half-life, distribution half-life, elimination half-life or combination thereof) of the biomolecule-polymer may be at least about 25% greater, at least about 30% greater, at least about 40% greater, at least about 50% greater, at least about 60% greater, at least about 70% greater, at least about 80% greater, at least about 90% greater, at least about 100% greater, at least about 200% greater, at least about 300% greater, at least about 400% greater, or at least 500% greater than the in vivo half-life of the biomolecule when the biomolecule has not been conjugated to a polymer according to methods of the invention.

Improved stability may also manifest as an increased shelf life of the biomolecule, for example by reducing aggregation of the biomolecules. For example, after storage at 4° C. or 20° C. for a period of about one month, about three months or about a year, the biomolecule-polymer conjugate may show less than about 10%, less than about 20%, less than about 30%, less than about 40%, less than about 50%, less than about 60%, less than about 70%, less than about 80%, or less than about 90% of the aggregation that occurs when the biomolecule has not been conjugated to a polymer according to methods of the invention.

The improved solubility may manifest as an improvement in the solubility of the biomolecule-conjugate, such that the solubility of the biomolecule-polymer conjugate is at least about 25% greater, at least about 30% greater, at least about 40% greater, at least about 50% greater, at least about 60% greater, at least about 70% greater, at least about 80% greater, at least about 90% greater, or at least about 100% greater than the solubility of the biomolecule that has not been modified according to methods of the invention. Aggregation of biomolecules, such as proteins and polypeptides, may also be controlled or reduced by improving solubility of the biomolecule, polypeptide or protein according to methods of the invention The improvement in pharmacokinetics may include an improvement in one or more of the following: liberation of the biomolecule-polymer conjugate when administered in a formulation, absorption into the body, dispersion or dissemination of the biomolecule-polymer conjugate throughout the fluids and tissues of the body, and metabolism of parent compounds into daughter metabolites. For example, the conjugate may effect a reduction in metabolism of an active compound, or may stimulate metabolism of an inactive compound to form active metabolites and a reduced rate of excretion of an active compound from the body.

The improvement in immunogenicity may manifest as an improvement reduction in the immune response to a biomolecule, such that the biomolecule-polymer conjugate or polypeptide-polymer conjugate evokes at least about a 10% reduction, at least about a 20% reduction, at least about a 30% reduction, at least about a 40% reduction, at least about a 50% reduction, at least about a 60% reduction, at least about a 70% reduction, or at least about a 80% reduction in the immune response against the conjugate.

The in vivo biodistribution of the biomolecule-polymer conjugate, such as a polypeptide-polymer conjugate, to a cell, tissue, organ or disease site, such as a tumor or arterial plaque, may be increased compared with the biodistribution of the non-conjugated biomolecule. Biodistribution as used herein means the extent to which the conjugates accumulate in a cell, tissue, organ or disease site. For example, the biodistribution of the biomolecule-conjugate to a cell, tissue, organ or disease site may be at least about 10%, at least about 20%, at least about 25%, at least about 30%, at least about 40%, at least about 50%, at least about 60%, at least about 70%, at least about 80%, at least about 90%, at least about 100%, at least about 125%, at least about 150%, at least about 200%, at least about 300%, at least about 400%, or at least about 500% greater compared with the biomolecule not conjugated to a polymer.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Materials Used in Examples 1-17

All molecular biology reagents were purchased from New England Biolabs, unless otherwise specified. All chemical reagents were purchased from Sigma Aldrich and used as received, unless otherwise specified.

Example 1

GFP-Srt-ELP Cloning, Expression and Purification

The gene for GFP (SEQ ID NO: 7) was PCR-amplified from an available GFP-containing pET32b(+) vector using the forward and reverse primers:

```
GFP-F:
                                   (SEQ ID NO: 8)
5' TTCCCCTCTAGAAATAATTTTGT 3'

GFP-R:
                                   (SEQ ID NO: 9)
3' CTACTTGACATGTTGCAGCTGCCGCCACCCCG

TCGAACGGCCTTTGGCCGCCATTCGAAACGAAC 5'
```

Figure 3:
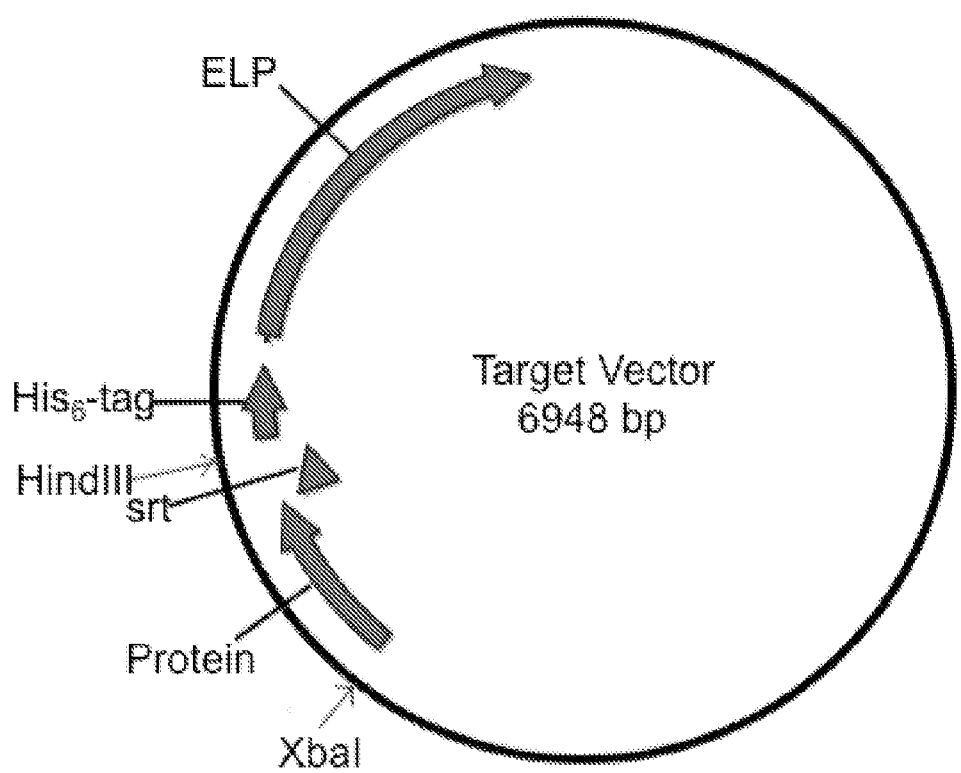
FIG. 3: Drawing depicting vector map of target vector.

The vector map of the target vector is shown in FIG. 3 (not to scale).

The GFP-F primer (SEQ ID NO: 8) was designed to anneal at the RBS site immediately upstream of the target GFP sequence and includes an XbaI site for cloning into the target vector (FIG. 3). The GFP-R primer (SEQ ID NO: 9) was designed to anneal to the C terminus of GFP (SEQ ID NO: 7) and includes an overhang that codes for a Gly$_4$Ser linker (SEQ ID NO: 10) and the 'LPETG' SrtA recognition sequence (SEQ ID NO: 2) as well as a HindIII site for cloning into the target vector.

The GFP-srt fragment was amplified in two 50 µL PCR reactions, each containing 25 µL GoTaq green master mix, 10 µmol each of forward and reverse primers, 0.25 µL template and nuclease-free water in a total volume of 50 µL. The PCR reaction conditions were: 95° C. for 2 min for initial denaturation, followed by 40 cycles at 95° C. for 30 s, 52° C. for 30 s, and 72° C. for 1 min. The resulting 'GFP-srt' PCR product was purified using a PCR purification kit and visualized on a 1% agarose gel stained with SYBR® Safe DNA stain. 1.5 µg of the GFP product was then digested with 2 µL each of XbaI and HindIII in 1×NEB buffer 2 and 1× bovine serum albumin (BSA) for 1.5 h at 37° C. and then purified using a PCR purification kit (QIAquick, QIAGEN).

A previously constructed pET25b(+) vector encoding a protein-srt-His6-ELP fusion gene was used as the target vector. In this vector, the protein-srt insert was flanked by XbaI and HindIII restriction sites followed by codons that encode a His6-tag, a thrombin cleavage site and an ELP with a sequence of (VPGXG)$_{90}$, where X represents alanine (A), glycine (G) and valine (V) (SEQ ID NO: 4) at 2:3:5 molar ratio. 1.5 µg of this target vector was digested with 2 µL each of XbaI and HindIII in 1×NEB buffer 2 with 1×BSA for 1.5 h at 37° C., enzymatically dephosphorylated with 1 µL CIP for 15 min to 1 h at 37° C. (to prevent self-circularization of the vector), and then purified using a PCR purification kit (QIAquick, QIAGEN).

The 'GFP-srt' PCR insert (5 µL) was ligated into the target vector (3 µL) using 4 µL of T4 ligase in 1× T4 ligase buffer and nuclease-free water in a total volume of 20 µL. The ligation mixture was incubated at room temperature for 1 h, and BL21 (DE) cells were then transformed with 7 µL of the ligation mixture for 15 min in an ice-water bath, heat-shocked at 42° C. for 30 s, and returned to the ice-water mixture for another 2 min. The cells were recovered in SOC media while horizontally shaking at 200 rpm at 37° C. for 40-60 min, and were then plated on TB agarose plates containing 100 µg/mL ampicillin (Calbiochem). Several clones were grown overnight in 3 mL TB media supplemented with 100 µg/mL ampicillin, and the plasmids were isolated by a miniprep plasmid purification kit (Qiagen) for DNA sequence verification.

Expression and purification of the fusion protein was carried out using modified techniques (Gao, W., et al. A. Proc. Natl. Acad. Sci. 2010, 107, 16432; Meyer, D. E., et al. Nat. Biotechnol. 1999, 14, 1112). Briefly, cells were cultured in Terrific Broth (TB, Mo Bio Laboratories, Inc.) supplemented with 100 µg/mL of ampicillin at 37° C. Once the optical density at 600 nm (OD600) of the culture reached 0.6, Isopropyl β-D-1-thiogalactopyranoside (IPTG, AMRESCO) was added to a final concentration of 0.5 mM to induce overnight expression. Cells were harvested 15 h post induction by centrifugation at 700×g for 10 min and were lysed by sonication on a Misonex Ultrasonic Liquid Processor (Qsonica, LLC.) at amplitude 85 for 3 min. Nucleic acids non-chromatographic purification were removed from the crude extract by addition of 1% v/v polyethyleneimine (PEI, Acros) followed by centrifugation at 4° C. at 21,000×g for 10 min.

The ELP tag enable of the fusion by Inverse Transition Cycling (ITC), a non-chromatographic method we have developed for the purification of ELP fusion proteins that takes advantage of their inverse phase transition behavior. After triggering the inverse phase transition of the fusion by addition of 1M NaCl, the aggregated proteins were collected by centrifugation at 21,000×g for 10 min at ~35° C. The pellet was then resolubilized in cold PBS and the resulting solution was centrifuged at 4° C. at 21,000×g for 10 min to remove any remaining insoluble material. The last two steps were repeated, typically three or four times, until satisfactory purity was achieved as verified by SDS-PAGE. In the final step, the protein was resolubilized in sortase buffer (50 mM Tris-HCl, 150 mM NaCl, 10 mM $CaCl_2$, pH 7.5) in preparation for sortase catalyzed initiator attachment (SCIA). Protein concentration and yield were assessed on an ND-1000 Nanodrop Spectrophotometer (Thermo Scientific) by UV-vis absorption spectroscopy.

Example 2

Sortase Cloning, Expression and Purification

The gene for SrtA with a 59 N-terminal amino acid truncation (previously shown to not affect its transpeptidase activity) (SEQ ID NO: 5, encoded by SEQ ID NO: 11) and an N-terminal His6-tag in a pET15b vector was transformed into BL21 *E. coli* cells. Expression of protein and cell lysis was carried out identically as for the GFP-srt-ELP fusion protein. The SrtA fusion protein was purified by immobilized metal affinity chromatography (IMAC) on HisPur™ cobalt spin columns (Thermo Scientific) and following the manufacturer protocol. Briefly, the cell lysate was mixed with equal volume of equilibration buffer (50 mM sodium phosphate, 300 mM sodium chloride, 10 mM imidazole; pH 7.4) and was loaded onto a pre-equilibrated HisPur™ column. After rotating the loaded columns at 4° C. for 30 min to maximize binding, unbound proteins were eluted by centrifugation at 700×g for 2 min. Additional equilibration washes were performed until absorbance measurement at 280 nm of the eluent reached baseline as monitored on a ND-1000 Nanodrop Spectrophotometer. Concentration and yield at each step were calculated from the absorbance measurements. The bound $(His)_6$-SrtA fusion protein was eluted by centrifugation at 700×g for 2 min in elution buffer (50 mM sodium phosphate, 300 mM sodium chloride, 150 mM imidazole; pH 7.4). Typically the first two elution washes were collected and were solvent exchanged by overnight dialysis against sortase buffer in preparation for further use.

Example 3

ATRP Initiator Synthesis

Figure 4:
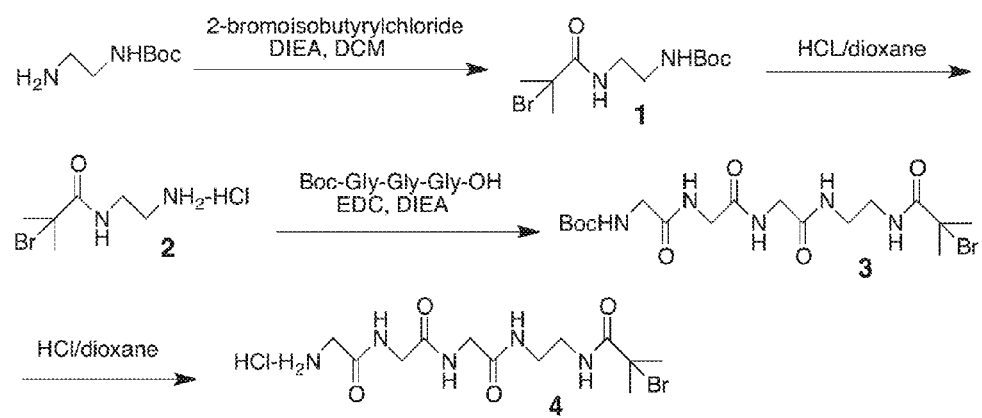
FIG. 4: Schematic illustration of the synthesis of ATRP initiator N-(2-(2-(2-(2-aminoacetamido)acetamido)acetamido)ethyl)-2-bromo-2-methylpropanamide (AEBMP) (Gao, W., et al. *Proc. Natl. Acad. Sci.* 2009, 36, 15231).

FIG. 4 shows the pathway for the synthesis of ATRP initiator N-(2-(2-(2-(2-aminoacetamido)acetamido)acetamido)ethyl)-2-bromo-2-methylpropanamide (AEBMP) (Gao, W., et al. *Proc. Natl. Acad. Sci.* 2009, 36, 15231).

tert-butyl (2-(2-bromo-2-methylpropanamido)ethyl)carbamate (1) as shown in FIG. 4 was synthesized as follows: Over a period of 15 min, 2-bromoisobutyryl bromide (3.9 mL, 31.2 mmol) was added to a NaCl/ice cooled bath solution of N-Boc-ethylenediamine (5.01 g, 31.2 mmol) and diisopropylethylamine (6 mL, 34 mmol, 1.1 eq.) in anhydrous dichloromethane (35 mL). After 1 h, the ice bath was removed and the reaction was allowed to warm to room temperature and stirring was continued for 18 h. Silica gel (~10 g) was added and the mixture was concentrated to dryness under reduced pressure on a rotary evaporator. Flash column chromatography (RediSepRf SiO2 (80 g), 100% $CH_2Cl_2 \rightarrow 50\%$ ethyl acetate (EtOAc) in $CH_2Cl_2$) gave 1 as an off-white solid (7.36 g, 75%). $^1$H NMR ($CDCl_3$, 300 MHz): δ 7.2 (bs, 1H), 4.91 (bs, 1H), 3.33 (m, 4H), 1.93 (s, 6H), 1.43 (s, 9H). $^{13}$C NMR ($CDCl_3$, 300 MHz): δ 172.9, 157.1, 80.1, 61.9, 42.0, 40.0, 32.5, 28.6. EIMS m/z: 331 ([M+Na]$^+$), 333 ([M+Na]$^+$).

N-(2-aminoethyl)-2-bromo-2-methylpropanamide hydrochloride (2) as shown in FIG. 4 was synthesized as follows: A solution of 1 (7.36 g, 23.8 mmol) in 4 M HCl in 1,4-dioxane (64 mL, 256 mmol) was stirred at room temperature for 1 h. The reaction mixture was concentrated to dryness on a rotary evaporator and further dried under high vacuum using a vacuum manifold connected to a vacuum pump, giving an off-white solid. The solid was triturated under diethyl ether ($Et_2O$, 3×100 mL) and the supernatant was removed by careful decantation. The insoluble material was dried under reduced pressure on a rotary evaporator giving 2 as a pale solid (5.8 g, 99%). $^1$H NMR ($CD_3OD$, 300 MHz): δ 8.36 (bs, 1H), 3.65 (bs, 1H), 3.51 (s, 2H), 3.09 (s, 2H), 1.94 (s, 6H). $^{13}$C NMR ($CD_3OD$, 300 MHz): δ 174.3, 58.9, 39.3, 37.8, 30.7. EIMS m/z: 209 ([M−Cl]$^+$), 211 ([M−Cl]$^+$).

tert-butyl (14-bromo-14-methyl-2,5,8,13-tetraoxo-3,6,9,12-tetraazapentadecyl)carbamate (3) as shown in FIG. 4 was synthesized as follows: Diisopropylethylamine (10.4 mL, 60 mmol, 2.5 eq.) was added in one portion to an ice-bath cooled suspension of 2 (5.8 g, 23.8 mmol), Boc-Gly-Gly-Gly-OH (6.9 g, 23.8 mmol), and EDC (6.84 g, 36 mmol, 1.5 eq.) in anhydrous $CH_2Cl_2$ (80 mL). The mixture was stirred overnight (16 h) then diluted with $CH_2Cl_2$ (80 mL). Insoluble material was isolated by vacuum filtration and the filter cake was washed sequentially with $H_2O$ (100 mL), cold MeOH (3×20 mL), $Et_2O$ (2×100 mL) and dried in vacuo giving 3 as a white powder (9.14 g, 80%) $^1$H NMR ($CDCl_3$, 300 MHz): δ 4.15-4.10 (m, 4H), 3.89 (s, 2H), 3.72 (m, 4H), 1.91 (s, 6H), 1.43 (s, 9H). $^{13}$C NMR (CDCl3, 300 MHz): δ 172.4, 168.9, 164.5, 156.8, 79.5, 52.8, 44.9, 44.4, 44.1, 38.2, 29.3, 25.2. EIMS m/z: 503 ([M+Na]$^+$), 505 ([M+Na]$^+$).

N-(2-(2-(2-(2-aminoacetamido)acetamido)acetamido)ethyl)-2-bromo-2-methylpropanamide hydrochloride (4) as shown in FIG. 4 was synthesized as follows: A solution of 3 (9.0 g, 18.8 mmol) in 4 M HCl in 1,4-dioxane (80 mL, 320 mmol) was stirred at room temperature for 1 h. The reaction mixture was diluted with $Et_2O$ (300 mL). Insoluble material was collected and dried by vacuum filtration, giving the product as a white powder (7.7 g, 98%). $^1$H NMR (CD3OD, 500 MHz): δ 4.20 (m, 4H), 3.85 (s, 2H), 3.70 (m, 4H), 1.92 (s, 6H). ($CDCl_3$, 300 MHz): δ 171.0, 169.8, 166.5, 163.8, 52.6, 43.3, 42.7, 38.8, 30.3. EIMS m/z: 380 ([MH−Cl]$^+$), 382 ([MH−Cl]$^+$).

Example 4

Sortase Catalyzed Initiator Attachment and Product Separation

A reaction mixture consisting of GFP-srt-ELP, SrtA, and AEBMP at a 2:1:60 ratio in sortase buffer was incubated at 37° C. for 5 h. Post reaction, a reverse His-tag purification was used to isolate the GFP-C-Br macroinitiator, by exploiting the fact that the macroinitiator is the only species in the mixture without a His6-tag. Equilibration and elution washes were done as described above. The first two equilibration washes containing the eluted GFP-C-Br were collected and solvent exchanged by overnight dialysis against PBS in preparation for use. A control reaction was done by replacing AEBMP with Gly$_3$, while keeping all other conditions the same. The resulting GFP-C-Gly$_3$ was used as negative control in the subsequent in situ ATRP reaction.

Example 5

In Situ ATRP from GFP-C-Br and Conjugate Purification

ATRP reactions were performed using conditions described previously with minor changes. (Gao et al. *Proc. Natl. Acad. Sci.* 2010, 107, 16432; Gao et al. *Proc. Natl. Acad. Sci.* 2009). OEGMA (MW=500) was eluted through a column packed with aluminum oxide to remove the polymerization inhibitor. Three sets of reaction conditions were attempted and the parameters are summarized in Table 1.

TABLE 1

ATRP reaction conditions for reactions (Rxn) 1, 2, and 3.

| | GFP-C-Br (μmol/eqv) | CuCl (μmol/eqv) | CuCl$_2$ (μmol/eqv) | HMTETA (μmol/eqv) | OEGMA (μmol/eqv) | time |
|---|---|---|---|---|---|---|
| Rxn 1 | 0.2/1 | 5.1/25 | 15.0/75 | 25.0/125 | 110/550 | 30 m |
| Rxn 2 | 0.2/1 | 5.1/25 | 11.1/55 | 20.0/100 | 220/1100 | 30 m |
| Rxn 3 | 0.2/1 | 5.1/25 | 11.1/55 | 20.0/100 | 440/2200 | 2 h |

Polymerization was typically carried out by first mixing specified amounts of CuCl, CuCl$_2$, and 1,1,2,7,10,10-hexamethyltriethylenetetramine (HMTETA) in 100 μL MilliQ water until all reagents were completely dissolved and then topping up with 400 μL PBS. A second solution was prepared by adding OEGMA to 2 mL of 100 μM GFP-C-Br in PBS. The two solutions were degassed by bubbling separately with argon for 30 min using a Schlenk line, after which the first solution was quickly transferred into the second solution by a cannula. Polymerization was allowed to proceed for a specified time at room temperature under argon and was quenched by bubbling with air. An initial separation of the conjugate from the small MW reagents was carried out by gel filtration on disposable PD-10 columns (GE Life Science) before subsequent purification and characterization.

Example 6

Sodium Dodecyl Sulfate Polyacrylamide Gel Electrophoresis (SDS-PAGE) and Initiator Attachment Efficiency Samples were prepared in Laemmli loading dye containing 5% v/v β-mercaptoethanol. After brief heating at 98° C., the samples were loaded onto precast 4-20% Tris-HCl gels (Bio-Rad). Gels were run at 130 V and 400 mA for 55 min in 1× running buffer (25 mM Tris, 192 mM Glycine, and 0.1% SDS) on a Bio-Rad Mini-PROTEAN gel apparatus. Gels were stained with copper chloride.

To determine efficiency of SCIA, quantification of gel band intensity was performed using ImageJ. This method for quantification of the yield of initiator attachment to GFP (SEQ ID NO: 7) is valid because we do not expect that attachment of the initiator to GFP should alter its staining by the dye. For each SDS-PAGE gel, bands in each lane were defined in ImageJ and converted into intensity profile plots using a built-in function, where each band was assigned a corresponding peak. After defining the baseline for each peak, band intensities were computed by calculating the area under each peak. Values were then imported into Excel (Microsoft) for analysis.

Because the errors involved in sample loading can be significant when the product of a sortase cleavage reaction is normalized to a standard amount of GFP-srt-ELP loaded in a separate lane, the yield of each SCIA reaction was calculated by internal normalization, wherein we assume that the intensity of the products of a sortase cleavage reaction sums to that of the parent fusion construct it was derived from. Hence, the band intensity of the initial amount of GFP-srt-ELP used in each reaction was determined by summing up all of its products after reaction, namely residual unreacted GFP-srt-ELP, cleaved ELP, and transpeptidized GFP-C-Br. The % unreacted product is thus the band intensity of unreacted GFP-srt-ELP divided by the sum of all products and multiplied by 100, and % transpeptidation is thus 100%—% unreacted. A very faint band slightly above 50 kDa could also be observed upon close inspection, which corresponds to an intermediate species of the reaction, where SrtA is linked to the C-terminus of GFP via a thioacyl bond. The presence of SrtA in this species makes its staining not directly comparable to that of the other species, so that the intensity of this bad was not incorporated into the overall calculation of reaction yield. However, including it in the sum of intensities and taking its percentage showed that this intermediate only comprised <1% of the overall intensity at most (Table 2), so that omitting it in the calculation of % transpeptidation yield does not significantly change the results.

Table 2 shows initiator attachment efficiency (% transpeptidation) of SCIA determined by SDS-PAGE gel band quantification averaged across five SCIA reactions. The intensity of initial GFP-srt-ELP was determined by summing intensities of unreacted GFP-srt-ELP, cleaved ELP, and transpeptidized GFP-C-Br. The percentage unreacted was calculated as the fraction of unreacted GFP-srt-ELP divided by sum of the three bands and multiplying by 100. The percentage transpeptidized was calculated as 100%— percentage unreacted. A very faint GFP-SrtA intermediate band was also observed in all reactions, but only comprised of up to ~1% in all cases. Because the presence of Sortase A in the intermediate alters its staining compared to the other three species, making direct quantitative manipulation difficult, its intensity was excluded from the calculation. Percentage transpeptidation was 96.3±1.5%.

TABLE 2 initiator attachment efficiency (% transpeptidation) of SCIA.

| | Intensity | | | | | | % Intensity | | |
|---|---|---|---|---|---|---|---|---|---|
| | Unreacted | | | Total | GFP- | | | | |
| | GFP-srt-ELP | Cleaved ELP | GFP-C-Br | w/o intermediate | SrtA intermediate | Total w/ intermediate | % intermediate | % Unreacted | % Transpeptidation |
| SCIA #1 | 203.7 | 1726.3 | 1810.2 | 3740.2 | 40.6 | 3780.8 | 1.1 | 5.4 | 94.6 |
| SCIA #2 | 268.3 | 5899.2 | 6970.4 | 13137.9 | 87.4 | 13225.3 | 0.7 | 2.0 | 98.0 |
| SCIA #3 | 505.6 | 4990.1 | 4971.3 | 10466.9 | 101.8 | 10568.7 | 1.0 | 4.8 | 95.2 |
| SCIA #4 | 207.8 | 3783.8 | 4209.0 | 8200.6 | 61.1 | 8261.6 | 0.7 | 2.5 | 97.5 |
| SCIA #5 | 538.9 | 6955.8 | 7421.7 | 14916.4 | 110.6 | 15026.9 | 0.7 | 3.6 | 96.4 |
| Mean ± Std. Dev. | | | | | | | | | 96.3 ± 1.5 |

Example 7

Liquid Chromatography Electrospray-Ionization Mass Spectrometry (LC/ESI-MS)

Samples at a concentration of 5 µM were first desalted by dialyzing against MilliQ water overnight. LC/ESI-MS was performed on an Agilent 1100 LC/MSD Quadrupole Mass Spectrometer. The instrument was calibrated with Cytochrome C and BSA. The ESI source was set to operate at 300° C. with a nebulizer gas pressure of 20 psi and a dry gas flow rate of 7 L/min. 1 µL of sample was separated by reverse phase chromatography on a Zorbax SB-C18 column (Agilent) at 20%-80% acetonitrile/water gradient and a flow rate of 60 µL/min. Spectra were acquired in positive ion mode over the mass to charge range (m/z) of 400-1,600. Theoretical MW of GFP-C-Br was calculated using Molecular Weight Calculator (v. 6.49, Pacific Northwest National Laboratory, ncrr.pnl.gov/software).

Example 8

Nano-Flow Liquid Chromatography Electrospray Ionization Tandem Mass Spectrometry (LC/MS-MS)

100 µL of ~8 µM sample was loaded on to a 0.5 mL ZebaSpin desalting column (Thermo Scientific) for solvent exchange into 50 mM ammonium bicarbonate, pH 8.0, supplemented with 0.1% Rapigest SF surfactant (Waters Corp), by washing the loaded column with 300 µL of the solvent solution four times. The sample was then reduced with 5 mM dithiolthreitol for 30 min at 70° C. and free sulfhydryls were alkylated with 10 mM iodoacetamide for 45 min at room temperature. Proteolytic digestion was accomplished by the addition of 500 ng sequencing grade trypsin (Promega) directly to the resin with incubation at 37° C. for 18 h. Supernatant was collected following a 2 min centrifugation at 1,000 rpm, acidified to pH 2.5 with TFA and incubated at 60° C. for 1 h to hydrolyze remaining Rapigest surfactant. Insoluble hydrolyzed surfactant was cleared by centrifugation at 15,000 rpm for 5 min and the sample was then dried by vacuum centrifugation.

The dried sample was resuspended in 20 µL 2% acetonitrile, 0.1% formic acid, and subjected to chromatographic separation on a Waters NanoAquity UPLC equipped with a 1.7 µm BEH130 C18 75 µm I.D.×250 mm reversed-phase column. The mobile phase consisted of (A) 0.1% formic acid in water and (B) 0.1% formic acid in acetonitrile. Following a 1 µl injection, peptides were trapped for 5 min on a 5 µm Symmetry C18 180 µm I.D.×20 mm column at 20 µL/min in 99.9% A. The analytical column (BEH130) was then switched in-line and a linear elution gradient of 5% B to 40% B was performed over 60 min at 400 nl/min. The analytical column was connected to a fused silica PicoTip emitter (New Objective, Cambridge, Mass.) with a 10 µm tip orifice and coupled to a Waters Synapt G2 HDMS QToF mass spectrometer through an electrospray interface. The instrument was operated in a data-dependent mode of acquisition in resolution mode with the top three most abundant ions selected for MS/MS using a charge state dependent CID energy setting with a 60 s dynamic exclusion list employed.

Mass spectra were processed with Mascot Distiller (Matrix Science) and were then submitted to Mascot searches (Matrix Science) against a SwissProt_*Ecoli* database appended with the custom *Aequorea victoria* GFP sequence with 10 ppm precursor and 0.04 Da product ion mass tolerances. Static mass modifications corresponding to carbamidomethylation on Cys residues, dynamic mass modifications corresponding to the ATRP initiator N-(2-(2-(2-(2-aminoacetamido)acetamido)acetamido)ethyl)-2-bromo-2-methylpropanamide (AEBMP), and oxidation of Met residues were included. Searched spectra were imported into Scaffold v4.0 (Proteome Software) and scoring thresholds were set to yield a minimum of 99% protein confidence (implemented by the PeptideProphet algorithm) based on decoy database searches. A minimum of two unique peptides from each protein were required for identification. Extracted ion chromatograms of the expected C-terminal tryptic peptide modified by AEBMP were performed in MassLynx (v4.1) at a 20 ppm mass accuracy window and experimental isotope distributions of the triply charged precursor ion was compared to a theoretical isotope distribution modeled in Molecular Weight Calculator.

Example 9

Size Exclusion Chromatography (SEC) and Conjugation Efficiency

Analytical SEC was performed on a Shimadzu HPLC system equipped with a UV-vis detector (SPD-10A VP) operating at 280 nm and a fluorescence detector (RF-10Axl) set at 460 nm excitation and 507 nm emission. 30 µL of samples at ~25 µM concentration were separated on a Protein KW-803 column (with a guard column) using Tris-HCl buffer (0.1M Tris-HCl, pH 7.4) as mobile phase at 25° C. and a flow rate of 0.5 mL/min. Preparative SEC to purify the conjugates was performed on an AKTA system (GE Healthcare) equipped with a photodiode detector set at 280 nm and a HiLoad 26/600 Superdex 200 PG column using PBS as mobile phase at 4° C. and a flow rate of 3 mL/min.

To determine conjugation efficiency of in situ ATRP from the C-terminus of GFP, area under the curve (AUC) of the GFP-C-poly(OEGMA) conjugate peak and the residual unreacted GFP-C-Br macroinitiator peak in the chromatogram of each polymerization reaction mixture were computed by EZStart software (v. 7.4, Shimadzu). Sum of the areas of the two peaks corresponding to the macroinitiator and the conjugate in each chromatogram was regarded as 100% and % fraction of the conjugate peak was recorded as the conjugation efficiency of that particular polymerization reaction. Values from the three reactions were then used to calculate the mean and standard deviation of conjugation efficiency. The calculation was done for chromatograms detected by both UV-vis absorbance (Table 3) and fluorescence (Table 4).

Example 10

Size Exclusion Chromatography Multi-Angle Light Scattering (SEC-MALS)

The fluid line of the analytical HPLC system was connected downstream in series to a DAWN HELEOS II MALS detector followed by an Optilab T-rEX refractometer (both from Wyatt Technology). The system was calibrated with toluene and normalized with 2.0 mg/mL Bovine Serum Albumin (BSA). Samples were filtered with 0.1 µm filters before injection. The One-detector method involving only the refractometer was used due to low degree of UV absorbance detected when running poly(OEGMA) polymer. Online determination of dn/dc was performed using built-in method "dn/dc from peak" under the assumption of 100% mass recovery. The assumption was verified by confirming that mass recovered as measured by online UV detection at 280 nm and mass injected as measured by offline UV absorbance at 280 nm using Nanodrop Spectrophotometer were in close agreement. The full recovery of sample through the column was likely due to presence of the stealth poly(OEGMA) polymer on the conjugates that minimized binding to the column. The actual mass injected was determined by lyophilization followed by weighing, and the number was entered into ASTRA (v. 6.0, Wyatt Technology) to compute dn/dc values of the conjugates. All results were analyzed using ASTRA 6.0.

Example 11

Dynamic Light Scattering (DLS)

DLS was performed on a DynaPro Plate Reader (Wyatt Technology). Samples were prepared at 25 µM and filtered with 0.1 µm filters before analysis. The instrument was operating at a laser wavelength of 831.95 nm, a scattering angle of 90° C. and at 25° C. Data were analyzed in Dynals mode using Dynamics 6.12.0.3.

Example 12

Fluorescence Spectroscopy

Fluorescence spectra were recorded on a CARY Eclipse fluorescence spectrophotometer (Varian) in scan mode at 25° C. The fluorescence of samples at a concentration of 20 µM was measured with an excitation wavelength of 460 nm and the emission intensity was recorded from 485-530 nm.

Example 13

Production of Sortase a Substrate

As shown in FIG. 1 and set forth in Examples 14-17, a ternary fusion protein, abbreviated as "GFP-srt-ELP", was recombinantly expressed to serve as the sortase substrate. Here, "srt" stands for the native SrtA recognition sequence "LPETG" (SEQ ID NO: 2) and ELP refers to an environmentally responsive elastin-like polypeptide (ELP; SEQ ID NO: 4) that was included in the fusion to enable easy purification of the ternary fusion by inverse transition cycling (ITC), a non-chromatographic protein purification method. The recognition sequence was deliberately located between the protein and the ELP, so that transpeptidation by Sortase A not only attaches the initiator to GFP but also conveniently liberates the purification tag. As transpeptidation relies on the presence of the enzyme, cleavage did not begin until Sortase A was added in vitro. Very little, if any, of the protein is thus lost in vivo before purification, hence increasing the overall product yield.

Example 14

Results of SDS-PAGE Analysis of ITC Purification of GFP-srt-ELP

Figure 5:
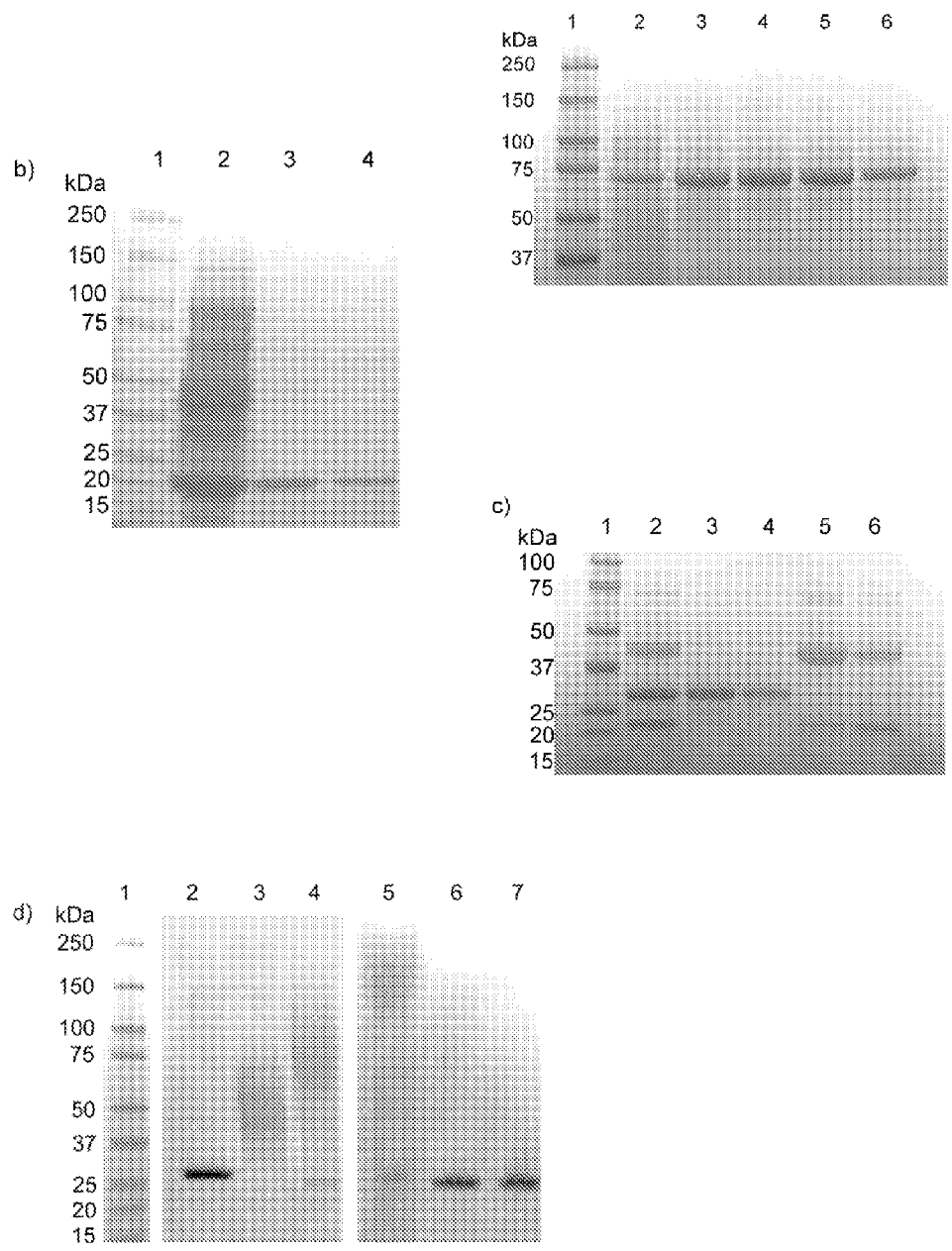
FIG. 5: Photograph showing SDS-PAGE analysis of a) GFP-srt-ELP purified by ITC (yield: ~240 mg/L of fermentation). Lane 1: marker, lane 2: E. coli lysate, lane 3: soluble protein after one ITC cycle, lane 4, after two ITC cycles, lane 5: after three ITC cycles, lane 6: after four ITC cycles. b) SrtA purified by $His_6$-tag purification (yield: ~135 mg/L of fermentation). Lane 1: marker, lane 2: E. coli lysate, lane 3: first elution wash with imidazole, lane 4: second elution wash with imidazole. c) GFP-C-Br purified by reverse $His_6$-tag purification. Lane 1: marker, lane 2: SCIA reaction mixture, lane 3: GFP-C-Br (without $His_6$-tag) in first elution without imidazole, lane 4: second elution without imidazole, lane 5: all other $His_6$-tagged components in first elution with imidazole, lane 6: second elution with imidazole. d) ATRP reaction products. Lane 1: marker, lane 2: GFP-C-Br macroinitiator before ATRP, lane 3: GFP-C-poly(OEGMA) conjugate from Rxn 1, lane 4: conjugate from Rxn 2, lane 5: conjugate from Rxn 3, lane 6: GFP-C-$Gly_3$ control after ATRP using Rxn 3 conditions, lane 7: GFP-C-Br physically mixed with free poly(OEGMA) synthesized using Rxn 3 conditions. Free poly(OEGMA) does not stain due to lack of charge.

SDS-PAGE was used to analyze the ITC purification of GFP-srt-ELP. As shown in FIG. 5(a), the only species that exhibited inverse transition behavior and thus was purified by ITC was GFP-srt-ELP. The lack of a free ELP band demonstrates that no premature in vivo cleavage occurred. The fusion protein was obtained at high purity with an excellent yield of ~300 mg/L from *E. coli* shaker flask culture.

In contrast, ~30% of the starting GFP-intein-ELP fusion protein was lost in the previously reported intein-mediated initiator attachment (IMIA) method. This is because the N→S acyl shift step in preparation for cleavage happens post-translationally in vivo, and the resulting linkage is prone to intracellular reduction in the reducing environment of the bacterial cytosol, which in turn exposes the C-terminal thioester and liberates the ELP. As a result, the prematurely cleaved protein cannot be purified by ITC and an additional purification step is required to remove the cleaved ELP. In contrast, sortase-catalyzed initiator attachment (SCIA) occurs solely in vitro, and hence offers greater degree of control over the reaction and product yield.

Sortase A carrying an N-terminal hexahistidine tag ($His_6$-tag) was also recombinantly expressed in *E. coli* in high purity and high yield (135 mg/L) by immobilized metal affinity chromatography (IMAC). FIG. 5(b). The ATRP initiator N-(2-(2-(2-(2-aminoacetamido)acet-amido)acet-amido)ethyl)-2-bromo-2-methylpropanamide (AEBMP, FIG. 1) was chemically synthesized with an N-terminal triglycine ($Gly_3$) motif serving as the nucleophile, as maximum reaction rates for Sortase-Mediated Ligation (SML) have been reported when two or more glycines are incorporated.

SCIA was then carried out at a GFP-srt-ELP:Sortase A:AEBMP ratio of 2:1:60 (FIG. 1b). SDS-PAGE analysis of the reaction mixture showed near complete disappearance of the GFP-srt-ELP band close to 67 kDa, and the appearance of two bands around 39 kDa and 28 kDa, corresponding to the cleaved ELP and the macroinitiator product, abbreviated as GFP-C-Br (FIG. 1a). A control reaction was done using Gly$_3$ as the nucleophile, to yield GFP-C-Gly$_3$ as negative control for subsequent ATRP reaction. Quantification of band intensity in SDS-PAGE showed that initiator attachment efficiency was near quantitative (~95% averaged across five samples, See Table 2 in Example 6).

Example 15

Purification and Analysis of the GFP-Initiator (Macroinitiator) Conjugates

Figure 6:
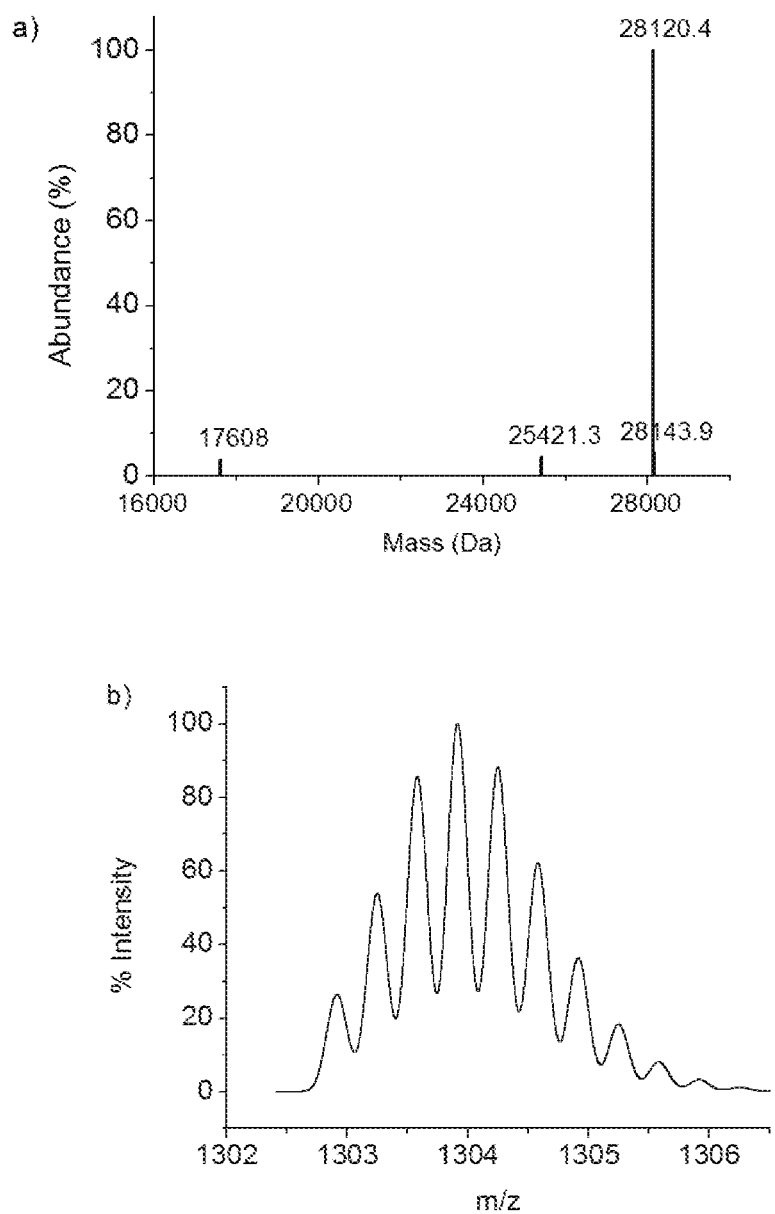
FIG. 6: Graphs depicting a) Deconvoluted LC/ESI-MS spectra of GFP-C-Br macroinitiator. Major peak at 28,120.4 Da agrees well with theoretical mass of 28,123.8 Da. b) Theoretical isotopic distribution of C-terminal peptide [DH-MVLLEFVTAAGITHGMDELYNVDGGGSLPET-"AEBMP"]$^{3+}$ (SEQ ID NO: 1-AEBMP) after tryptic digestion generated by Molecular Mass Calculator software (v. 6.49, Pacific Northwest National Laboratory, Richland, Wash.).

To purify GFP-C-Br, a His$_6$-tag was intentionally inserted between "srt" and ELP, such that upon transpeptidation by Sortase A, all species except GFP-C-Br carried a His$_6$-tag. Consequently, elution through an IMAC column yielded pure macroinitiator in the eluent while leaving all other unwanted species bound to the resin. SDS-PAGE analysis (FIG. 5c) indicated that all of the GFP-C-Br was recovered by this method. The purified GFP-C-Br was then characterized by liquid chromatography/electrospray-ionization mass spectrometry (LC/ESI-MS) to confirm initiator attachment (FIG. 6a). A major peak was detected at 28,120.4 Da, which closely agrees with the theoretical mass of 28,123.8 Da for GFP-C-Br. To prove site-specificity of initiator attachment, GFP-C-Br was subjected to trypsin digestion and the peptide fragments were analyzed by LC-MS/MS. Only the C-terminal peptide fragment was detected as a brominated cation and its experimental isotope distribution (FIG. 2b) showed nearly perfect overlap with its theoretical distribution (FIG. 6b). These results provided strong evidence that the brominated ATRP initiator was solely attached to the C-terminus of GFP by SrtA. Aside from the singly brominated C-terminal peptide, no other derivatives were detected. In SCIA however, the lack of any thiol group close to the initiator attachment site obviates byproduct formation through disulfide bonding, further contributing to higher product yield. Additionally, the absence of a thiol group also lowers the chance of dimerization of the macroinitiator.

Example 16

ATRP Growth of Polymers from GFP-C-Br Macroinitiators

Subsequently, in situ ATRP was performed to graft poly(OEGMA) from GFP-C-Br (FIG. 1c). Three sets of polymerization conditions (see Table 1 in Example 5) were investigated to synthesize conjugates of increasing molecular weights, denoted herein as Rxn 1, Rxn 2, and Rxn 3. Size exclusion chromatography (SEC) was performed after ATRP to characterize the polymerization product. SEC of the product with UV-vis absorbance detection at 280 nm (FIG. 2c) showed a single peak at an elution time of 20.6 min, corresponding to GFP-C-Br prior to polymerization. This peak greatly diminished after polymerization, and was accompanied by the emergence of peaks at 17.9 min, 15.9 min, and 13.3 min, corresponding to GFP-C-poly(OEGMA) conjugates in each of the three reactions. The results from UV-visible spectroscopic (UV/vis) detection were consistent with those from fluorescence detection (FIG. 7). Integration of peak areas showed that the conjugates constituted >90% of the polymerization product on average (Tables 3 and 4), indicating that in situ ATRP from GFP-C-Br proceeds with extremely high efficiency.

Table 3 shows the conjugation efficiency of in situ ATRP from C-terminus of GFP determined by AUC of HPLC chromatograms of three independent reactions detected by UV-vis absorbance at 280 nm. Area % was calculated by dividing area of an individual peak by total area (sum of the two) and multiplying by 100. Averaging area % values of GFP-C-poly(OEGMA) conjugates from three reactions gives conjugation efficiency of 95.0±2.2%.

TABLE 3

Conjugation efficiency of in situ ATRP detected by UV-vis absorbance at 280 nm.

| | Area | | | Area % | |
|---|---|---|---|---|---|
| | GFP-C—Br | GFP-C-poly(OEGMA) | Total | GFP-C—Br | GFP-C-poly(OEGMA) |
| Rxn #1 | 59151.0 | 813750.0 | 872901.0 | 6.8 | 93.2 |
| Rxn #2 | 70996.0 | 1202397.0 | 1273393.0 | 5.6 | 94.4 |
| Rxn #3 | 29056.0 | 1133247.0 | 1162303.0 | 2.5 | 97.5 |
| Mean ± Std. Dev. | | | | | 95.0 ± 2.2 |

Table 4 shows the conjugation efficiency of in situ ATRP from the C-terminus of GFP determined by AUC of HPLC chromatograms of three attempted reactions detected by fluorescence at 460 nm excitation and 507 nm emission. Area % was calculated by dividing area of individual peak by total area (sum of the two peaks) and multiplying by 100. Averaging the area % values of GFP-C-poly(OEGMA) conjugates from three reactions yielded a conjugation efficiency of 93.6±1.9%.

TABLE 4

Conjugation efficiency of in situ ATRP detected by fluorescence at 460 nm excitation and 507 nm emission.

| | Area | | | Area % | |
|---|---|---|---|---|---|
| | GFP-C—Br | GFP-C-poly(OEGMA) | Total | GFP-C—Br | GFP-C-poly(OEGMA) |
| Rxn #1 | 3235695.0 | 74156445.0 | 77392140.0 | 4.4 | 95.8 |
| Rxn #2 | 7885455.0 | 95738118.0 | 103623573.0 | 8.2 | 92.4 |
| Rxn #3 | 6046562.0 | 77048389.0 | 83094951.0 | 7.8 | 92.7 |
| Mean ± Std. Dev. | | | | | 93.6 ± 1.9 |

SDS-PAGE analysis provided additional evidence for the successful growth of poly(OEGMA) from GFP-C-Br (FIG. 5d). After each reaction, the band corresponding to GFP-C-Br (~28 kDa) decreased to a much lower intensity, accompanied by a new higher molecular weight band corresponding to the conjugate. In contrast, when the GFP-C-Gly3 control was used in the polymerization, or when GFP-C-Br was physically mixed with pre-synthesized poly(OEGMA), only a single band was observed around 28 kDa, proving that poly(OEGMA) was only grown in situ from the C-terminal initiator attached by SCIA.

Example 17

Characterization of Polymer-Polypeptide Conjugates

The conjugates were further characterized by light scattering. First, size exclusion chromatography multi-angle light scattering (SEC-MALS) was performed to determine the weight-average molecular weight (MW) and radius of gyration (Rg) of the conjugates. The Mw of GFP-C-Br measured 28,030 Da and the polydispersity index (PDI) was 1.01, consistent with the theoretical value of 28,123.8 Da and the expected monodispersity of the macroinitiator. The molecular weights of the three conjugates measured by SEC-MALS were 6.115×10$^4$ Da, 8.985×10$^4$ Da, and 2.631×10$^5$ Da, respectively, with corresponding PDI's of 1.23, 1.26, and 1.25.

Table 5 shows the light scattering characterizations of GFP-C-Br macroinitiator and GFP-C-poly(OEGMA) conjugates. MW, PDI and $R_g$ were measured by SEC-MALS and $R_h$ was measured by DLS.

TABLE 5

Light scattering characterizations of GFP-C—Br macroinitiator and GFP-C-poly(OEGMA) conjugates.

|  | GFP-C—Br | Rxn 1 | Rxn 2 | Rxn 3 |
|---|---|---|---|---|
| $M_w$ (kDa) | 28.0 | 61.2 | 89.9 | 263.1 |
| PDI | 1.01 | 1.23 | 1.26 | 1.25 |
| $R_g$ (nm) | N/A* | N/A* | 10.6 | 19.2 |
| $R_h$ (nm) | 3.6 | 6.4 | 10.0 | 18.3 |
| $R_g/R_h$ | N/A | N/A | 1.06 | 1.05 |

*Below lower limit of detection of instrument.

Figure 8:
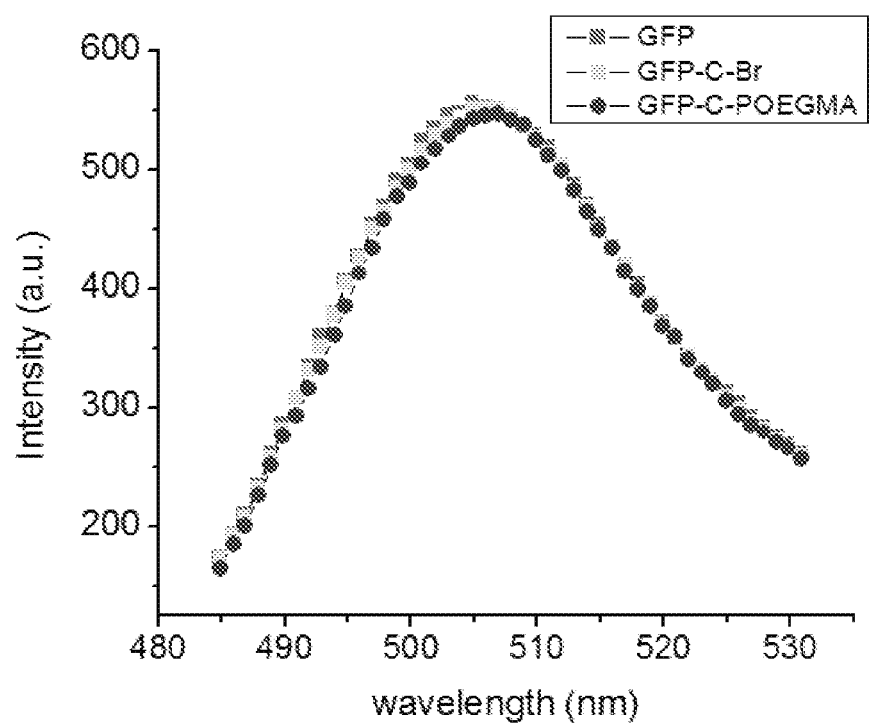
FIG. 8: Graph showing fluorescence spectrum of GFP before initiator attachment (dark squares), after initiator attachment (light squares), and after in situ ATRP (dark circles, ATRP at Rxn 3 conditions); all samples at 20 µM.

These results show that by tuning the ATRP conditions, conjugates can be synthesized from macroinitiators generated by SCIA with different molecular weights and fairly low polydispersity. The Rg's of GFP-C-Br and Rxn 1 conjugate could not be accurately determined by SEC-MALS, as they fell below the 10 nm lower limit of detection at a laser wavelength of 638 nm. $R_g$'s of the products of Rxn 2 and 3 were 10.6 nm and 19.2 nm, respectively. Next, the hydrodynamic radius ($R_h$) of each species was measured by dynamic light scattering (DLS). The Rh of GFP-C-Br was determined to be 3.6 nm. In situ growth of poly(OEGMA) from the macroinitiator resulted in an increase of the Rh to 6.4 nm, 10.0 nm, and 18.3 nm, for the three polymerization reactions, respectively. With both Rg and Rh available for Rxn 2 and 3, their corresponding $R_g/R_h$ ratios (p=form factor) were calculated, yielding values of 1.06 and 1.05, respectively. To put these values in perspective, for globular proteins is ~0.775, while that of monodisperse random coil polymer in theta solvent is 1.50. An increase in polymer polydispersity and the presence in a good solvent can increase ρ32. Thus, their p values suggest that the overall conformation of the GFP-C-poly(OEGMA) conjugates lies somewhere between that of their components. The conjugates could be easily and completely purified by preparative SEC. Fluorescence spectroscopy of unmodified GFP, GFP-C-Br, and purified GFP-C-poly(OEGMA) clearly shows that each step in the synthesis of the conjugate has minimal effect on the activity of the protein (FIG. 8).

Various features and advantages of the invention are set forth in the following claims.

SEQUENCES

SEQ ID NO: 1
amino acid
DHMVLLEFVTAAGITHGMDELYNVDGGGSLPET
* May be modified with AEBMP at the C-terminal end.

SEQ ID NO: 2
SrtA recognition sequence, amino acid
LPETG

SEQ ID NO: 3
SrtA recognition sequence, amino acid
LPXTG, wherein X is any amino acid SEQ ID NO: 4
an environmentally responsive elastin-like polypeptide (ELP), amino acid
(VPGXG)$_{90}$, where X represents alanine (A), glycine (G), or valine (V)

SEQ ID NO: 5
Truncated S. aureus SrtA, amino acid
GQAKPQIPKDKSKVAGYIEIPDADIKEPVYPGPATPEQLNRGVSFAEENESLDDQNISIAGHT
FIDRPNYQFTNLKAAKKGSMVYFKVGNETRKYKMTSIRDVKPTDVGVLDEQKGKDKQLTLIT
CDDYNEKTGVWEKRKIFVATEVKALVT SEQ ID NO: 6
Full length wild-type S. aureus SrtA, amino acid
MKKWTNRLMTIAGVVLILVAAYLFAKPHIDNYLHDKDKDEKIEQYDKNVKEQASKDNKQQAK
PQIPKDKSKVAGYIEIPDADIKEPVYPGPATPEQLNRGVSFAEENESLDDQNISIAGHTFIDRP
NYQFTNLKAAKKGSMVYFKVGNETRKYKMTSIRDVKPTDVEVLDEQKGKDKQLTLITCDDY
NEKTGVWEKRKIFVATEVK SEQ ID NO: 7
GFP, amino acid
MSKGEELFTGVVPILVELDGDVNGHKFSVSGEGEGDATYGKLTLKFICTTGKLPVPWPTLVT
TFAYGVQCFSRYPDHMKRHDFFKSAMPEGYVQERTIFFKDDGNYKTRAEVKFEGDTLVNRI
ELKGIDFKEDGNILGHKLEYNYNSHNVYIMADKQKNGIKVNFKIRHNIEDGSVQLADHYQQN
TPIGDGPVLLPDNHYLSTQSVLSKDPNEKRDHMVLLEFVTAAGITHGMDELYK -continued

| SEQUENCES |
|---|

SEQ ID NO: 8
GFP forward primer (GFP-F), polynucleotide, synthetic
5'-TTCCCCTCTAGAAATAATTTTGT-3'

SEQ ID NO: 9
GFP reverse primer (GFP-R), polynucleotide, synthetic
3'-CTACTTGACATGTTGCAGCTGCCGCCACCCCCGTCGAACGGCCTTTGGCCGCCATTCG
AAACGAAC-5'

SEQ ID NO: 10
Gly$_4$Ser linker, amino acid, synthetic
GGGGS

SEQ ID NO: 11
Truncated *S. aureus* SrtA, polynucleotide
GGCCAAGCTAAACCTCAAATTCCGAAAGATAAATCGAAAGTGGCAGGCTATATTGAAAT
TCCAGATGCTGATATTAAAGAACCAGTGTATCCAGGACCAGCAACACCTGAACAATTAA
ATAGAGGTGTAAGCTTTGCAGAAGAAAATGAATCACTAGATGATCAAAATATTTCAATTG
CAGGACACACTTTCATTGACCGTCCGAACTATCAATTTACAAATCTTAAAGCAGCCAAA
AAGGTAGTATGGTGTACTTTAAAGTTGGTAATGAAACACGTAAGTATAAAATGACAAGTA
TAAGAGATGTTAAGCCTACAGATGTAGGAGTTCTAGATGAACAAAAAGGTAAAGATAAA
CAATTAACATTAATTACTTGTGATGATTACAATGAAAAGACAGGCGTTTGGGAAAAACGT
AAAATCTTTGTAGCTACAGAAGTCAAAGCACTAGTTACT SEQ ID NO: 12
Full length wild-type *S. aureus* SrtA, polynucleotide
ATGAAAAAATGGACAAATCGATTAATGACAATCGCTGGTGTAGTACTTATCCTAGTGGC
AGCATATTTGTTTGCTAAACCACATATCGATAATTATCTTCACGATAAAGATAAAGATGAA
AAGATTGAACAATATGATAAAAATGTAAAAGAACAGGCGAGTAAAGACAATAAGCAGCA
AGCTAAACCTCAAATTCCGAAAGATAAATCAAAAGTGGCAGGCTATATTGAAATTCCAGA
TGCTGATATTAAAGAACCAGTATATCCAGGACCAGCAACACCTGAACAATTAAATAGAG
GTGTAAGCTTTGCAGAAGAAAATGAATCACTAGATGATCAAAATATTTCAATTGCAGGAC
ACACTTTCATTGACCGTCCGAACTATCAATTTACAAATCTTAAAGCAGCCAAAAAAGGTA
GTATGGTGTACTTTAAAGTTGGTAATGAAACACGTAAGTATAAAATGACAAGTATAAGAG
ATGTTAAGCCAACAGATGTAGAAGTTCTAGATGAACAAAAAGGTAAAGATAAACAATTAA
CATTAATTACTTGTGATGATTACAATGAAAAGACAGGCGTTTGGGAAAAACGTAAAATCT
TTGTAGCTACAGAAGTCAAATAA

---

| SEQUENCE LISTING |
|---|

<160> NUMBER OF SEQ ID NOS: 12

<210> SEQ ID NO 1
<211> LENGTH: 33
<212> TYPE: PRT
<213> ORGANISM: Unknown
<220> FEATURE:
<223> OTHER INFORMATION: peptide

<400> SEQUENCE: 1

Asp His Met Val Leu Leu Glu Phe Val Thr Ala Ala Gly Ile Thr His
1               5                   10                  15

Gly Met Asp Glu Leu Tyr Asn Val Asp Gly Gly Gly Ser Leu Pro Glu
            20                  25                  30

Thr

<210> SEQ ID NO 2
<211> LENGTH: 5
<212> TYPE: PRT
<213> ORGANISM: Unknown
<220> FEATURE:
<223> OTHER INFORMATION: peptide

<400> SEQUENCE: 2

Leu Pro Glu Thr Gly
1               5

```
<210> SEQ ID NO 3
<211> LENGTH: 5
<212> TYPE: PRT
<213> ORGANISM: Unknown
<220> FEATURE:
<223> OTHER INFORMATION: peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Leu Pro Xaa Thr Gly
1               5

<210> SEQ ID NO 4
<211> LENGTH: 5
<212> TYPE: PRT
<213> ORGANISM: Unknown
<220> FEATURE:
<223> OTHER INFORMATION: peptide
<220> FEATURE:
<221> NAME/KEY: misc_feature
<222> LOCATION: (4)..(4)
<223> OTHER INFORMATION: Xaa is alanine (A), glycine (G), or valine (V)

<400> SEQUENCE: 4

Val Pro Gly Xaa Gly
1               5

<210> SEQ ID NO 5
<211> LENGTH: 152
<212> TYPE: PRT
<213> ORGANISM: Staphylococcus aureus

<400> SEQUENCE: 5

Gly Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Pro Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asp Val Lys Pro Thr Asp Val Gly Val Leu Asp
            100                 105                 110

Glu Gln Lys Gly Lys Asp Lys Gln Leu Thr Leu Ile Thr Cys Asp Asp
        115                 120                 125

Tyr Asn Glu Lys Thr Gly Val Trp Glu Lys Arg Lys Ile Phe Val Ala
    130                 135                 140

Thr Glu Val Lys Ala Leu Val Thr
145                 150

<210> SEQ ID NO 6
<211> LENGTH: 206
<212> TYPE: PRT
<213> ORGANISM: Staphylococcus aureus

<400> SEQUENCE: 6
```

```
Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
            195                 200                 205

<210> SEQ ID NO 7
<211> LENGTH: 238
<212> TYPE: PRT
<213> ORGANISM: Unknown
<220> FEATURE:
<223> OTHER INFORMATION: peptide

<400> SEQUENCE: 7

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Ala Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160
```

```
Ile Lys Val Asn Phe Lys Ile Arg His Asn Ile Glu Asp Gly Ser Val
            165                 170                 175
Gln Leu Ala Asp His Tyr Gln Gln Asn Thr Pro Ile Gly Asp Gly Pro
        180                 185                 190
Val Leu Leu Pro Asp Asn His Tyr Leu Ser Thr Gln Ser Val Leu Ser
    195                 200                 205
Lys Asp Pro Asn Glu Lys Arg Asp His Met Val Leu Leu Glu Phe Val
210                 215                 220
Thr Ala Ala Gly Ile Thr His Gly Met Asp Glu Leu Tyr Lys
225                 230                 235
```

<210> SEQ ID NO 8
<211> LENGTH: 23
<212> TYPE: DNA
<213> ORGANISM: Artificial sequence
<220> FEATURE:
<223> OTHER INFORMATION: synthetic

<400> SEQUENCE: 8
ttcccctcta gaaataattt tgt                                        23

<210> SEQ ID NO 9
<211> LENGTH: 66
<212> TYPE: DNA
<213> ORGANISM: Artificial sequence
<220> FEATURE:
<223> OTHER INFORMATION: synthetic

<400> SEQUENCE: 9
caagcaaagc ttaccgccgg tttccggcaa gctgccccca ccgccgtcga cgttgtacag    60
ttcatc                                                              66

<210> SEQ ID NO 10
<211> LENGTH: 5
<212> TYPE: PRT
<213> ORGANISM: Unknown
<220> FEATURE:
<223> OTHER INFORMATION: synthetic

<400> SEQUENCE: 10

```
Gly Gly Gly Gly Ser
1               5
```

<210> SEQ ID NO 11
<211> LENGTH: 456
<212> TYPE: DNA
<213> ORGANISM: Staphylococcus aureus

<400> SEQUENCE: 11
ggccaagcta aacctcaaat tccgaaagat aaatcgaaag tggcaggcta tattgaaatt    60
ccagatgctg atattaaaga accagtgtat ccaggaccag caacacctga caattaaat   120 agaggtgtaa gctttgcaga agaaaatgaa tcactagatg atcaaaatat ttcaattgca   180
ggacacactt tcattgaccg tccgaactat caatttacaa tcttaaagc agccaaaaaa    240 ggtagtatgg tgtactttaa agttggtaat gaaacacgta agtataaaat gacaagtata   300
agagatgtta agcctacaga tgtaggagtt ctagatgaac aaaaaggtaa agataaacaa   360
ttaacattaa ttacttgtga tgattacaat gaaagacag gcgtttggga aaacgtaaa    420 atctttgtag ctacagaagt caaagcacta gttact                             456

```
<210> SEQ ID NO 12
<211> LENGTH: 621
<212> TYPE: DNA
<213> ORGANISM: Staphylococcus aureus

<400> SEQUENCE: 12
atgaaaaaat ggacaaatcg attaatgaca atcgctggtg tagtacttat cctagtggca      60
gcatatttgt ttgctaaacc acatatcgat aattatcttc acgataaaga taaagatgaa     120
aagattgaac aatatgataa aaatgtaaaa gaacaggcga gtaaagacaa taagcagcaa     180
gctaaacctc aaattccgaa agataaatca aaagtggcag gctatattga aattccagat     240
gctgatatta aagaaccagt atatccagga ccagcaacac ctgaacaatt aaatagaggt     300
gtaagctttg cagaagaaaa tgaatcacta gatgatcaaa atatttcaat tgcaggacac     360
actttcattg accgtccgaa ctatcaattt acaaatctta aagcagccaa aaaaggtagt     420
atggtgtact ttaaagttgg taatgaaaca cgtaagtata aaatgacaag tataagagat     480
gttaagccaa cagatgtaga agttctagat gaacaaaaag gtaaagataa acaattaaca     540
ttaattactt gtgatgatta caatgaaaag acaggcgttt gggaaaaacg taaaatcttt     600
gtagctacag aagtcaaata a                                                621
```

What is claimed is:

1. A method of making polypeptide-polymer conjugates having one or more altered pharmacological properties from a plurality of polypeptides having C-termini, the method comprising:
   a) contacting the plurality of polypeptides with a sortase and an initiator agent under conditions that permit attachment of the initiator agent to the C-terminus to form a plurality of macroinitiators; and
   b) incubating the plurality of macroinitiators with a monomer under conditions that permit free-radical polymerization to occur from the initiator agent to form polypeptide-polymer conjugates, such that at least about 25% of the polypeptides have a conjugated polymer initiated solely from the C-terminus,
   wherein the polypeptide-polymer conjugates have an altered pharmacological property selected from at least one of (i) an in vivo half-life that is at least 25% greater compared with the in vivo half-life of the plurality of polypeptides; and (ii) an in vivo biodistribution to a tissue, organ or disease site that is at least 25% greater than the in vivo biodistribution of the plurality of polypeptides.

2. The method of claim 1, wherein the plurality of polypeptides comprise one or more peptides or protein therapeutic agents selected from an interferon, insulin, monoclonal antibody, blood factor, colony stimulating factor, growth hormone, interleukin, growth factor, therapeutic vaccine, calcitonin, tumor necrosis factors (TNF), TNF-related apoptosis-inducing ligand (TRAIL), glucagon-like peptide-1 (GLP-1), vasoactive intestinal peptide (VIP), beta-trophin, enzyme, uricase, adenosine deaminase, asparaginase, and single chain antibodies.

3. The method of claim 1, wherein the monomer comprises at least one of an acrylate, methacylate, acrylamide, and methacrylamide.

4. The method of claim 1, wherein the polymer has side chains comprising moieties selected from oligoethylene glycol, betaine, carboxybetaine, sulfobetaine, phosphorylcholine, sarcosine or a combination thereof.

5. The method of claim 1, wherein the free-radical polymerization comprises at least one of atom transfer radical polymerization (ATRP) and reversible addition-fragmentation chain transfer (RAFT).

6. The method of claim 1, wherein the polypeptide comprises a sortase recognition site, a His-tag, an elastin-responsive polypeptide, or a combination thereof.

7. The method of claim 6, wherein the sortase recognition site comprises LPXTG (SEQ ID NO: 3), wherein X is any amino acid.

8. The method of claim 1, wherein the sortase is Sortase A (SEQ ID NO: 5 or SEQ ID NO: 6).

9. The method of claim 1, wherein the plurality of polypeptides and monomer are incubated with a catalyst in step (b).

10. The method of claim 1, wherein the polypeptide-polymer conjugates have an in vivo half-life that is at least 80% greater than the in vivo half-life of the polypeptides.

11. The method of claim 1, wherein at least about 50% of the polypeptides have a conjugated polymer initiated solely from the C-terminus.

12. The method of claim 1, wherein at least about 75% of the polypeptides have a conjugated polymer initiated solely from the C-terminus.

13. The method of claim 1, wherein at least about 90% of the polypeptides have a conjugated polymer initiated solely from the C-terminus.

14. The method of claim 1, further comprising separating the polypeptide-polymer conjugates formed in step b from the unreacted macroinitiators, wherein the yield of polypeptide-polymer conjugates is at least about 50% of the total conjugates and macroinitiators which are separated.

15. The method of claim 14, wherein the yield of polypeptide-polymer conjugates is at least about 75%.

16. The method of claim 14, wherein the yield of polypeptide-polymer conjugates is at least about 85%.

17. The method of claim 14, wherein the polypeptide-polymer conjugates are separated by chromatography.

18. The method of claim 17, wherein the wherein the polypeptide-polymer conjugates are separated by size-exclusion chromatography.

* * * * *